US007361517B2

(12) United States Patent
Ahearn et al.

(10) Patent No.: US 7,361,517 B2
(45) Date of Patent: Apr. 22, 2008

(54) REAL TIME METHOD OF DETECTING ACUTE INFLAMMATORY CONDITIONS

(75) Inventors: Joseph M. Ahearn, Sewickley, PA (US); Susan M. Manzi, Wexford, PA (US)

(73) Assignee: University of Pittsburgh, Pittsburgh, PA (US)

( * ) Notice: Subject to any disclaimer, the term of this patent is extended or adjusted under 35 U.S.C. 154(b) by 97 days.

(21) Appl. No.: 11/101,898

(22) Filed: Apr. 8, 2005

(65) Prior Publication Data

US 2005/0282234 A1 Dec. 22, 2005

Related U.S. Application Data

(60) Provisional application No. 60/579,621, filed on Jun. 14, 2004, provisional application No. 60/560,986, filed on Apr. 9, 2004.

(51) Int. Cl.
G01N 33/53 (2006.01)
(52) U.S. Cl. ...................... 436/811; 435/7.1; 435/7.92; 436/501; 436/518
(58) Field of Classification Search ................ 435/7.1, 435/7.2, 7.92–7.94; 436/501, 518, 164, 811
See application file for complete search history.

(56) References Cited

U.S. PATENT DOCUMENTS

| 2003/0139353 | A1* | 7/2003 | Jackson et al. ................ 514/27 |
| 2003/0158083 | A1* | 8/2003 | Peters ............................ 514/1 |
| 2005/0037441 | A1 | 2/2005 | Ahearn et al. |
| 2005/0042602 | A1 | 2/2005 | Ahearn et al. |

FOREIGN PATENT DOCUMENTS

| WO | WO 94/10571 A1 | 5/1994 |
| WO | WO 03/022223 A2 | 3/2003 |

OTHER PUBLICATIONS

Beutler et al., Williams Hematology, Fifth Edition, 1995, pp. 353-356.*
Brown, Hematology: Principles and Procedures, Sixth Edition, p. 37 and pp. 111-113, 1993.*
Alexander, Elaine, et al., "Serum complement activation in central nervous system disease in sjogren's syndrome;" The American Journal of Medicine, Oct. 1988, vol. 85, No. 4, abstract only.
Atkinson, J.P., et al., "Origin of the Fourth Component of Complement Related Chido and Rodgers Blood Group Antigens;" 1988; Compliment; vol. 5; pp. 65-76.
Bombardier, Claire, et al., "Derivation of the Sledai A Disease Activity Index for Lupus Patients;" Arthritis Rheum, Jun. 1992, vol. 35; No. 6; pp. 630-640.
Buyon, J.P., et al., "Assessment of disease activity and impending flare in patients with systemic lupus erythematosus;" Arthritis Rheum, 1992, vol. 35, pp. 1028-1037.

Chudwin, D., et al., "Activation of the Alternative Complement Pathway by Red Blood Cells from Patients with Sickle Cell Disease;" Clinical Immunology and Immunopathology, May 1994, vol. 71, No. 2, pp. 199-202.
Corvetta, Angelo, et al.; "Low Number of Complement C3b/C4b Receptors (CR1) on Erythrocytes from Patients with Essential Mixed Cryoglobulinemia, Systemic Lupus Erythematosus and Rheumatoid Arthritis: Relationship with Disease Activity, Anticardiolipin Antibodies, Complement Activation and Therapy;" 1981, J. Rheumatol., vol. 18, pp. 1021-1025.
Cosio, F.G., et al., "The high prevalence of severe early post-transplant renal allograft pathology in hepatitis C positive recipients;" Transplantation, Oct. 27, 1996, vol. 62, No. 8, abstract only.
Falk, R.J.., et al., "Radioimmunoassay of the attack complex of complement in serum from patients with systemic lupus erythematosus;" N. Engl. J. Med., 1985, vol. 312, pp. 1594-1599.
Freysdottir, Jona, et al.;"A flow cytometric assay for measuring complement receptor 1 (CR1) and the complement fragments C3d and C4d on erythrocytes;"1991, Journal of Immunological Methods, vol. 142, pp. 45-52.
Jouvin, Marie-Helene et al.; "Decreased Expression of C3b Receptor (CR1) on Erythrocytes of Patients with Systemic Lupus erythematosus Contrasts with Its Normal Expression in Other Systemic Diseases and Does Not Correlate with the Occurrence or Severity of SLE Nephritis;" Complement;1986, vol. 3, pp. 88-96.
Lach-Trifilieff, Estelle, et al., "Complement Receptor 1 (CD35) on Human Reticulocytes: Normal Express in Systemic Lupus Erythematosus and HIV-Infected Patients;" The Journal of Immunology, vol. 162, No. 12, Jun. 1999, pp. 7549-7554.
Lamprecht, P., et al. "Immunological and clinical follow up of hepatitis C virus associated cryoglobulinaemic vasculitis;" Annals of the Rheumatic Diseases, Apr. 2001, vol. 60, pp. 385-390.
Liang, Matthew H., et al., "Reliability and Validity of Six Systems for the Clinical Assessment of Disease Activity in Systemic Lupus Erythematosus," Arthritis Rheum, Sep. 1989, vol. 32; No. 9; pp. 1107-1118.
Manzi, Susan, et al.; "Measurement of Erythrocyte C4d and Complement Receptor 1 in Systemic Lupus Erythematosus;" Nov. 2004, Arthritis & Rheumatism, vol. 50, No. 11, pp. 3596-3604.

(Continued)

Primary Examiner—Long V. Le
Assistant Examiner—Gary W. Counts
(74) Attorney, Agent, or Firm—Gwen R. Acker Wood; Eckert Seamans Cherin & Mellott, LLC

(57) ABSTRACT

This invention relates to the diagnosis and/or monitoring of patients with inflammatory diseases or conditions, including systemic lupus erythematosus, particularly for diagnosis of the acute stage of the disease, including methods and kits for carrying out this activity. This disclosure presents the surprising discovery that levels of complement pathway components on reticulocytes can be used to diagnose, monitor, or predict the occurrence of acute episodes of chronic inflammatory diseases or conditions.

12 Claims, 11 Drawing Sheets

OTHER PUBLICATIONS

Manzi, Susan, et al.; "*Sensitivity and Specificity of Plasma and Urine Complement Split Products as Indicators of Lupus Disease Activity*;" 1996, Arthritis & Rheumatism, vol. 39, No. 7, pp. 1178-1188.

Manzi, Susan, et al.; "*New insights into complement: a mediator of injury and marker of disease activity in systemic lupus erythematosus*;" 2004, Lupus, vol. 13, pp. 1-6.

Accn. No. 85046338 Medline. McCarthy, T., et al., "*Intrauterine devices and pelvic inflammatory disease*;" Australian and New Zealand Journal of Obstetrics and Gynecology, May 1984, vol. 24, No. 2, pp. 106-110, Abstract.

McGeer, P.L. et al.; "*Reactions of the Immune System in Chronic Degenerative Neurological Diseases*;" The Canadian Journal of Neurological Sciences; 1991, vol. 18; pp. 376-379.

Accn. No. 90367342 Medline. Meliconi, R., et al., "*Complement activation products in idiopathic pulmonary fibrosis: relevance of fragment Ba to disease severity*;" Clinical Immunology and Immunopathology, Oct. 1990, vol. 57, No. 1, pp. 64-73, Abstract.

Navratil, J.S., et al., "*Apoptosis and autoimmunity: complement deficiency and systemic lupus erythematosus revisited*;" Curr. Rheumatol. Rep., 2000, vol. 2, pp. 32-38.

Ricker, D.M., et al., "*Serum C3 levels are diagnostically more sensitive and specific for systemic lupus erythematosus activity than are serum C4 levels*;" The Lupus Nephritis Collaborative Study Group, Am. J. Kidney Dis., 1991, vol. 18, pp. 678-685.

Ross, Gordon D. et al.; "*Disease-Associated Loss of Erythrocyte Complement Receptors (CR1, C3b Receptors) in Patients with Systemic Lupus Erythematosus and other Diseases Involving Auto antibodies and/or Complement Activation*;" 1985, Journal of Immunology, vol. 135, No. 3, pp. 2005-2014.

Senaldi, G., et al., "*Correlation of the activation of the fourth component of complement (C4) with disease activity in systemic lupus erythematosus*;" Ann. Rheum. Dis., 1988, vol. 47, pp. 913-917.

Sirois, M., et al., "*An Enzyme-linked Immunosorbent Assay for the Detection of Complement Components on Red Blood Cells*;" Am. Journ. Clin. Path., Jul. 1984, vol. 82, No. 1, pp. 67-73.

Tausk, Francisco, et al., "*The Expression of C3b Receptors in the Differentiation of Discoid Lupus Erythematosus and Systemic Lupus Erythematosus*;" Arthritis and Rheumatism, Jun. 1990, vol. 33, No. 6, pp. 888-892.

Tilley, C.A., et al., "*Localisation of Chido and Rodgers Determinants to the C4d Fragment of Human C4*;" Nature; Dec. 14, 1978; vol. 276; pp. 713-715.

Tsuboi, Y. et al.; "*Increased concentration of C4d complement protein in CSF in amyotrophic lateral sclerosis*"; Neurosurgery and Psychiatry 1994, vol. 57, pp. 859-861.

Yamada, T., et al. "*Complement-activated oligodendroglia: a new pathogenic entity identified by immunostaining with antibodies to human complement proteins C3d and C4d*;" Neuroscience Letters, 1990, vol. 112, pp. 161-166.

\* cited by examiner

REAL TIME METHOD OF DETECTING ACUTE INFLAMMATORY CONDITIONS

CROSS-REFERENCES TO RELATED APPLICATIONS

This application claims the benefit of U.S. Provisional Application No. 60/560,986, filed Apr. 9, 2004 and claims the benefit of U.S. Provisional Application No. 60/579,621, filed Jun. 14, 2004; both of which are herein in incorporated by reference in their entirety for all purposes.

STATEMENT AS TO RIGHTS TO INVENTIONS MADE UNDER FEDERALLY SPONSORED RESEARCH AND DEVELOPMENT

This invention was made with Government support under Grant Nos. RO1 HL-074335, RO1 AR-4676402, RO1 AR-46588, NCRR/GCRC MO1-RR-00056, K24 AR-02213, K23 AR-051044, awarded by the National Institutes of Health. The Government has certain rights in this invention.

FIELD OF THE INVENTION

This invention relates to the diagnosis and/or monitoring of patients with inflammatory diseases or conditions, including systemic lupus erythematosus, particularly for diagnosis of the acute stage of the disease, including methods and kits for carrying out this activity. This disclosure presents the surprising discovery that levels of complement pathway components on reticulocytes can be used to diagnose, monitor, or predict the occurrence of acute episodes of chronic inflammatory diseases or conditions.

BACKGROUND OF THE INVENTION

This invention relates to the diagnosis and/or monitoring of patients with an acute episode of an inflammatory disease or condition. In some embodiments the inflammatory disease or condition is systemic lupus erythematosus (SLE). The invention also provides means for predicting the onset of an acute episode of an inflammatory disease or condition, including SLE.

Monitoring disease activity is also problematic in caring for patients with inflammatory diseases or conditions. Chronic inflammatory diseases or conditions frequently progress in a series of flares, or periods of acute illness, followed by remissions. Over time, however, these flares can lead to irreversible organ damage. In order to minimize such damage, earlier and more accurate detection of disease flares would not only expedite appropriate treatment, but would reduce the frequency of unnecessary interventions. From an investigative standpoint, the ability to uniformly describe the "extent of inflammation" or activity of disease in individual organ systems or as a general measure is an invaluable research tool. Furthermore, a measure of disease activity can be used as a response variable in a therapeutic trial. Thus, there is a need for reliable methods to diagnose or predict the acute stage of inflammatory disease or condition, including SLE. The present invention meets these and other needs.

BRIEF SUMMARY OF THE INVENTION

This disclosure provides methods for diagnosing or monitoring an acute inflammatory episode of a chronic inflammatory disease or condition in an individual by (a) determining the level of a complement pathway component on a reticulocyte from the individual, and (b) comparing the complement pathway component level with a control level of complement pathway component, where a difference from the control level of the complement pathway component indicates that the individual has the acute inflammatory episode of the chronic inflammatory disease or condition. The level of more than one complement component can be determined and compared to a control level. For example, a ratio of complement pathway components can be determined and compared to a ratio of control complement pathway component levels. In some embodiments, an antibody specific for the complement pathway component is used to determine the level of the complement pathway component. In one embodiment, the level of the complement pathway component C4d is determined.

The disclosed methods can be used to diagnose or monitor an acute inflammatory condition in a number of chronic inflammatory diseases or conditions, e.g. systemic lupus erythematosus (SLE), hepatitis C infection, sickle cell anemia, complications of transplantation, and complications of pregnancy.

In one embodiment, an acute episode of SLE is diagnosed. For example, to diagnose or monitor an acute episode of SLE, the level of complement pathway component C4d on reticulocytes can be determined and compared to a level of complement component C4d on reticulocytes from a control. The level of complement component C4d can be determined using an antibody specific for C4d. A labeled C4d antibody can be used and, in some embodiments the C4d antibody is detected using flow cytometric analysis.

This disclosure also provides methods for predicting the occurrence of an acute inflammatory episode of a chronic inflammatory disease or condition in an individual by (a) determining the level of a complement pathway component on a reticulocyte from the individual, and (b) comparing the complement pathway component level with a control level of complement pathway component, where a difference from the control level of the complement pathway component indicates that the individual has the acute inflammatory episode of the chronic inflammatory disease or condition. The level of more than one complement component can be determined and compared to a control level. For example, a ratio of complement pathway components can be determined and compared to a ratio of control complement pathway component levels. In some embodiments, an antibody specific for the complement pathway component is used to determine the level of the complement pathway component. In one embodiment, the level of the complement pathway component C4d is determined.

The disclosed methods can be used to predict occurrence of an acute inflammatory condition in a number of chronic inflammatory diseases or conditions, e.g. systemic lupus erythematosus (SLE), hepatitis C infection, sickle cell anemia, complications of transplantation, and complications of pregnancy.

In one embodiment, an acute episode of SLE is predicted. For example, to predict an acute episode of SLE, the level of complement pathway component C4d on reticulocytes can be determined and compared to a level of complement component C4d on reticulocytes from a control. The level of complement component C4d can be determined using an antibody specific for C4d. A labeled C4d antibody can be used and, in some embodiments the C4d antibody is detected using flow cytometric analysis.

This disclosure describes and enables a kit for diagnosing, monitoring, or predicting an acute inflammatory episode of a chronic inflammatory disease or condition in an individual. The kit can include an antibody specific for a complement pathway component and a means for comparing a level of the complement pathway component to a control level of complement pathway component. A difference from the control level of the complement pathway component indicates that the individual has the acute inflammatory episode of the chronic inflammatory disease or condition. In some embodiment an acute episode of SLE is diagnosed, monitored, or predicted. The antibody can be fluorescently labeled, and in some embodiments, a monoclonal antibody is used.

This disclosure also provides a computer readable medium for diagnosing, monitoring, or predicting an acute inflammatory episode of a chronic inflammatory disease or condition in an individual. The computer readable medium can include (a) code for receiving data corresponding to a determination of complement pathway component on reticulocytes; (b) code for retrieving a reference value for complement pathway component on reticulocytes of individuals; and (c) code for comparing the data in (a) with the reference value in (b).

DETAILED DESCRIPTION OF THE INVENTION

Introduction

Figure 1:
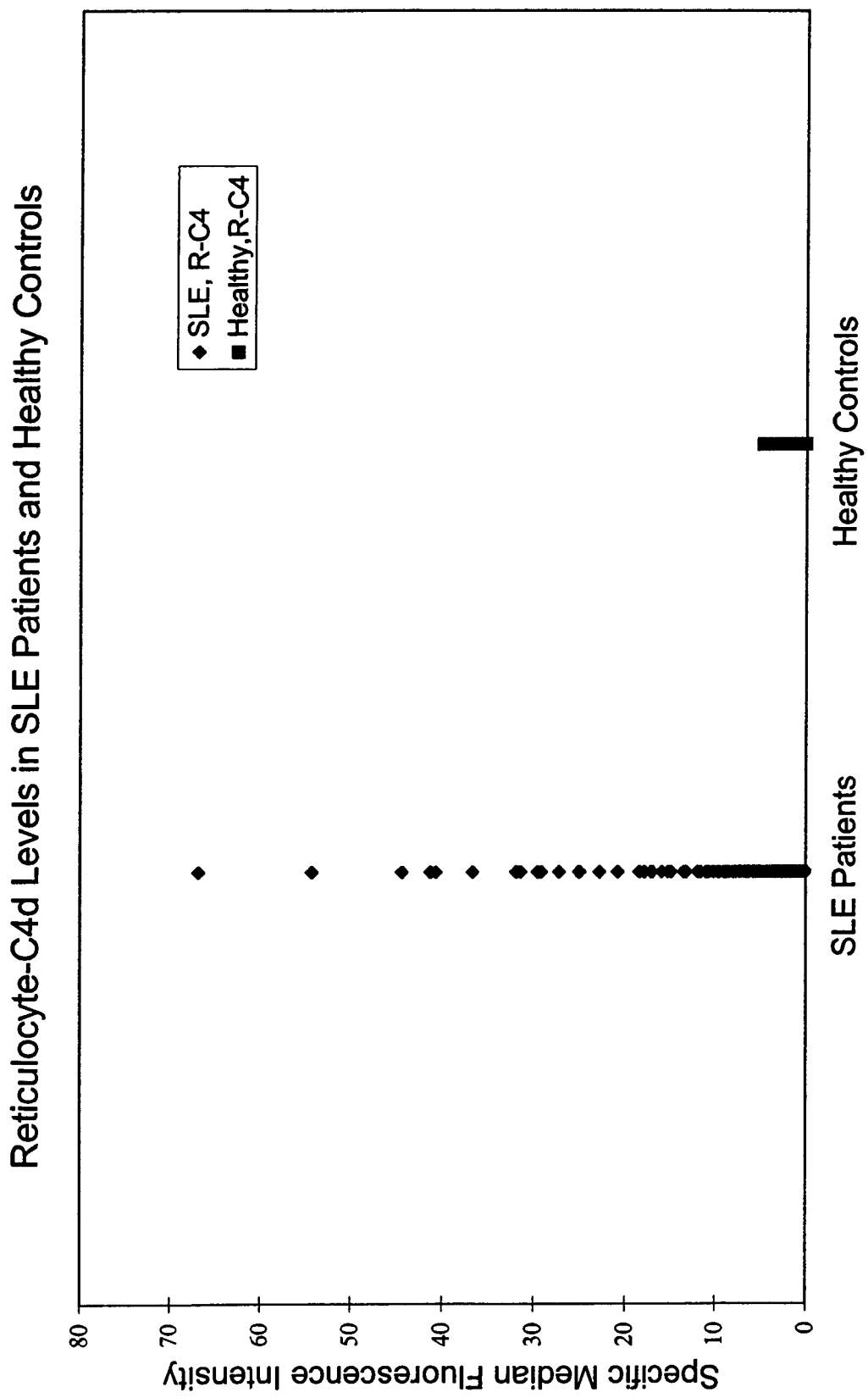
FIG. 1 provides a graph plotting the values of median fluorescence values for the patients with SLE and healthy controls. R-C4 refers to C4d levels on the surface of reticulocytes. Values for patients with SLE are shown on the left; values for healthy controls are shown on the right.

The methods of this invention enable the diagnosis and/or monitoring of acute episodes of chronic inflammatory diseases or conditions, including SLE. This disclosure presents the surprising discovery that levels of complement pathway components on reticulocytes can be used to diagnose, monitor, or predict the occurrence of acute episodes of chronic inflammatory diseases or conditions. Because acute episodes of chronic inflammatory diseases and conditions, e.g., SLE, are serious health problems, there is a need for relatively accurate and early diagnosis of these conditions. Likewise, the ability to monitor or to predict the occurrence of acute episodes inflammatory diseases or conditions is of great importance.

The invention involves determinations of the level of a complement pathway component on reticulocytes. In some embodiments, the level of complement pathway component C4d is determined.

In part, the methods of this invention are based on the discovery by the inventors that the level of C4d deposited on surfaces of immature red blood cells, i.e., reticulocytes, can serve as a diagnostic marker for an acute inflammatory episode resulting from SLE, a chronic inflammatory condition.

In diagnosing the occurrence, or predicted occurrence of an acute episode of a chronic inflammatory disease or condition, the level of a complement pathway component of reticulocytes in a sample is determined. The determination is then compared with the quantities of a complement pathway component found on reticulocytes of individuals not having a chronic inflammatory disease or condition, or of individuals who are not in the acute phase of a chronic inflammatory disease or condition. For example, a level of a complement pathway component such as C4d can be determined on a reticulocyte of a patient with SLE. The determination is then compared with the quantities of a complement pathway component found on reticulocytes of individuals not having SLE, or of individuals who are not in the acute phase of SLE, to diagnose, monitor or predict the occurrence of an acute episode or flare of SLE.

In monitoring disease activity of a patient with an acute episode of a chronic inflammatory disease or condition, the same determinations are made in the patient's blood sample, and are then compared with determinations of the quantities of a complement pathway component present on surfaces of reticulocytes in a sample obtained from the same patient in the past.

Another use of this invention is to monitor complement activation during the course of human diseases. Current state-of-the-art methods rely on measurement of serum or plasma levels of soluble complement C3 and/or C4. However there are known inadequacies with this approach. For example, C3 and C4 are parent molecules and are precursors to activation of the complement cascade. Increased hepatic and extra-hepatic synthesis of C3 and C4 can balance increased C3 and C4 catabolism during activation of the complement cascade resulting in misleading change or lack or change in serum levels. In addition, genetic deficiencies of C4 are well documented and result in abnormally low serum/plasma levels of C4 due to lack of synthetic capacity that can be misinterpreted as being due to increased C4 consumption during complement activation. The invention described herein is based upon measurement of protein products of complement activation such as C3d, C4d, and others that are attached to surfaces of circulating blood cells such as reticulocytes, and others. This enables monitoring levels of activation products as opposed to reactants, and eliminates the weaknesses inherent in measuring soluble C3 and C4 described above. Thus, levels of complement pathway components on reticulocytes can be determined and compared to control levels of complement pathway components in order to diagnose or monitor activation of the complement pathway.

Definitions

As used herein, an "inflammatory disease or condition" refers to any immune disease or condition that causes increased inflammation in an individual. An inflammatory disease or condition also refers to any infectious disease or condition that causes increased inflammation in an individual. In some embodiments the inflammatory disease or condition is a "chronic inflammatory disease or condition." A chronic inflammatory disease or condition is an inflammatory condition that does not resolve after a period of weeks, months or longer. Chronic inflammatory conditions can follow an acute inflammatory condition, or for some diseases or conditions can occur in the absence of an acute inflammatory disease or condition. An inflammatory disease or condition includes the following: systemic lupus erythematosus (lupus or SLE), rheumatoid arthritis, vasculitis (and its specific forms such as Wegener's granulomatosis), scleroderma, myositis, serum sickness, transplant rejection, sickle cell anemia, gout, complications of pregnancy such as pre-eclampsia, multiple sclerosis, cardiovascular disease, infectious disease such as hepatitis C virus infection, etc. Each of these diseases or conditions can also be described as chronic inflammatory diseases or conditions.

An "acute inflammatory episode" as used herein refers to an increased immune response. Symptoms of acute inflammation include redness, heat, swelling, pain, and loss of function, e.g., loss of joint movement. An acute inflammatory episode of a chronic inflammatory disease or condition differs from the typical symptoms of a chronic inflammatory disease or condition in the following ways. Frequently, during an acute inflammatory response the liver synthesizes acute phase proteins or acute phase reactants that are detectable in the blood stream. While the presence of acute phase reactants indicates that an acute inflammatory condition is occurring in the body, they are not diagnostic for a specific acute inflammatory episode. Acute phase reactants include C-reactive protein (CRP); alpha 1-antitrypsin; alpha 1-antichymotrypsin; alpha 2-macroglobulin; coagulation factors such as fibrinogen, fibrin, prothrombin, thrombin, factor VIII, and plasminogen; complement proteins, and serum amyloid protein. In addition, during an acute inflammatory episode, local inflammatory cells, e.g., neutrophils and macrophages, secrete a number of cytokines into the bloodstream, most notably IL-1, IL-6, IL-11, and TNF-alpha.

"Real time diagnosis" refers to diagnosis of an acute inflammatory episode while the inflammation or the acute inflammatory symptoms are occurring. Monitoring markers on reticulocytes provides real time diagnosis because reticulocytes are present for only 1-2 days before maturing into erythrocytes.

As used herein, a "reticulocyte" refers to an immature red blood cell. Reticulocytes are usually obtained by taking a blood sample from an individual. In some embodiment, a reticulocyte is isolated from a blood sample of an individual.

As used herein, the "complement pathway or system" refers to a complex network of more than 30 functionally linked proteins that interact in a highly regulated manner to provide many of the effector functions of humoral immunity and inflammation, thereby serving as the major defense mechanism against bacterial and fungal infections. This system of proteins acts against invasion by foreign organisms via three distinct pathways: the classical pathway (in the presence of antibody) or the alternative pathway (in the absence of antibody) and the lectin pathway. Once activated, the proteins within each pathway form a cascade involving sequential self-assembly into multimolecular complexes that perform various functions intended to eradicate the foreign antigens that initiated the response. For a review of the complement pathway, see, e.g., Sim and Tsiftsoglou, *Biochem. Soc. Trans.* 32:21-27 (2004).

The classical pathway is usually triggered by an antibody bound to a foreign particle. It consists of several components that are specific to the classical pathway and designated C1, C4, C2. Sequentially, binding of C1q to an antigen-antibody complex results in activation of C1r and C1s (both are serine proteases), and activated C1s cleaves C4 and C2 into, respectively, C4a and C4b and C2a and C2b. Fragments C4b and C2a assemble to form C4b2a, which cleaves protein C3 into C3a and C3b, which completes activation of the classical pathway. Fragments C4b and C3b are subject to further degradation by Factor I. This factor cleaves C4b to generate C4d and also cleaves C3b, to generate iC3b followed by C3d. Thus, activation of the classical pathway of complement can lead to deposition of a number of fragments, such as C4d, iC3b, and C3d, on immune complexes or other target surfaces. Such targets include cells circulating in the blood, e.g., lymphocytes and other white blood cells, erythrocytes and platelets.

Activation of the alternative complement pathway begins when C3b (or C3i) binds to e.g., the cell wall or other surface components of a microbe. Alternative pathway protein Factor B then combines with the cell-bound C3b to form C3bB. Factor D then splits the bound Factor B into Bb and Ba, forming C3bBb. A serum protein called properdin then binds to the Bb to form C3bBbP, which functions as a C3 convertase that lyses C3 into C3a and C3b.

The lectin complement pathway is mediated by mannan-binding lectin or mannan-binding protein (MBP). MBP is a protein that binds to the mannose groups found in many microbial carbohydrates. The MBP appears to be functionally equivalent to C1q in the classical complement pathway. Activation of the lectin pathway begins when MBP binds to the mannose groups of microbial carbohydrates. Two more lectin pathway proteins called MASP1 and MASP2 (functionally equivalent to C1r and C1s of the classical pathway) then bind to the MBP. The MASP1/MASP2/MBL complex forms an enzyme with activity similar to C1 of the classical complement pathway that is able to cleave C4 and C2 to form C4bC2a, a C3 convertase that lyses C3 into C3a and C3b. The C3 convertase cleaves and activates complement pathway components to form a membrane attack complex (MAC) that forms a pore in a bacterial cell wall, lysing the bacterial cell.

As used herein a "complement pathway component" includes proteins from the classical, alternative, and lectin complement pathways, e.g., C1, C4, C2, C3 and fragments thereof, e.g., C1q, C1r, C1s, C4a, C4b, C2a, C2b, C4bC2a, C3a, C3b, C4c, C4d, iC4b, C3d, C3i, C3dg. Also included are C5, C5b, C6, C7, C8, C9, C1inh, MASP1, MASP2, MBL, MAC, CR1, DAF, MCP, C4 binding protein (C4BP), protein factor H, Factor B, C3bB, Factor D, Bb, Ba, C3bBb, properdin, C3bBb, CD59, C3aR, C5aR, C1qR, CR2, CR3, and CR4, as well as other complement pathway components, receptors and ligands not listed specifically herein.

As used herein, a "control level of the complement pathway component" refers, in some embodiments, to a level of a complement pathway component on a cell from an individual who does not suffer from a chronic inflammatory disease or condition. A control level can also be determined by analysis of a population of individuals. In other embodiments, the control level of a complement pathway component is from an individual who does have a chronic inflammatory disease or condition, but is not experiencing an acute phase of the disease. In some embodiments, the control level of a complement pathway component is from the same individual for whom a diagnosis is sought or whose disease is being monitored, but is obtained at a different time. A control level of a complement pathway component can also be used as a reference value for a complement pathway component in a computer readable medium.

As used herein, "a difference from a control level" refers to a difference that is statistically significant, as determined by statistical analysis methods used by those in the art. A difference from a control level refers to a statistically significant difference between a control level of a complement pathway component and a level of a complement pathway component from an individual for whom diagnosis or other information is sought, i.e., an experimental level. Those of skill will recognize that many methods are available to determine whether a difference is statistically significant and the particular method used is not limiting to the invention.

As used herein, "systemic lupus erythematosus", "SLE", or "lupus" is the prototypic autoimmune disease resulting in multiorgan involvement. This anti-self response is characterized by autoantibodies directed against a variety of nuclear and cytoplasmic cellular components. These autoantibodies bind to their respective antigens, forming immune complexes which circulate and eventually deposit in tissues. This immune complex deposition and consequential activation of the complement system causes chronic inflammation and tissue damage.

SLE progresses in a series of flares, or periods of acute illness, followed by remissions. The symptoms of an SLE flare, which vary considerably between patients and even within the same patient, include malaise, fever, symmetric joint pain, and photosensitivity (development of rashes after brief sun exposure). Other symptoms of SLE include hair loss, ulcers of mucous membranes, inflammation of the lining of the heart and lungs which leads to chest pain and synovitis, a painful inflammation of synovial fluid. Red blood cells, platelets and white blood cells can be targeted in lupus, resulting in anemia and bleeding problems. More seriously, immune complex deposition and chronic inflammation in the blood vessels can lead to kidney involvement and occasionally failure requiring dialysis or kidney transplantation. Since the blood vessel is a major target of the autoimmune response in SLE, premature strokes and heart disease are not uncommon. Over time, however, these flares can lead to irreversible organ damage.

As used herein, "systemic sclerosis or scleroderma" is a chronic disorder of connective tissue characterized by inflammation and fibrosis and by degenerative changes of the blood vessels, skin, gastrointestinal tract, lung, heart and kidney. Scleroderma is a disabling and life-threatening disease. Criteria have been developed for the classification of patients with scleroderma (Masi A T, Rodnan G P, Medsger T A Jr, et al. Preliminary criteria for the classification of systemic sclerosis (scleroderma). *Arth Rheum* 1980; 23:581-590). These criteria are intended for description of large series of patients in research studies and not for diagnosis of individual patients. The major criterion is sclerodermatosus skin changes (thickening of the skin) in any location proximal to the digits. With the addition of any two or three minor criteria [sclerodactyly (skin thickening involving the digits), digital pitting scars, bibasilar pulmonary interstitial fibrosis] the sensitivity for the diagnosis increases. However, nearly 10% of individuals with definite scleroderma do not satisfy these criteria (Medsger T A Jr. Comment on scleroderma criteria cooperative study. In: Black C M, Myers A R, eds. Current Topics in Rheumatology: Systemic Sclerosis. New York: Gower Medical Publishing, 1985:16-17).

The status of a scleroderma patient or "severity" of his/her disease at a given time represents some combination of irreversible changes or "damage" and potentially reversible changes or "activity." Inflammation, early in the course of disease, leads to fibrosis and scarring later. If one could accurately detect the inflammatory activity, early intervention may prevent future irreversible damage. However, it is often difficult for clinicians to distinguish disease damage from disease activity. In part, this may be because clinical evidence of activity can be extremely subtle. In addition, there is no reliable laboratory marker of inflammation. Cross-sectional and longitudinal assessment of disease damage and activity are essential in evaluating the natural history of disease and in measuring the effectiveness of interventions, both in individual patients and in clinical trials. A review of this disorder can be found in Medsger T A Jr. Systemic sclerosis (scleroderma): clinical aspects. In: Koopman W J, ed. Arthritis and Allied Conditions. 13th ed. Philadelphia: Lea and Febiger, 1997: 1433-1464.

As used herein, the term "hepatitis" relates generally to a disease or condition characterized by an inflammation of the liver. The term "hepatitis C" relates more specifically to an infection by the hepatitis C virus (HCV). The introduction of the hepatitis C virus into a host is usually by parenteral means and typically marked by blood to blood contact. In many instances, the infection by HCV is chronic, and can lead to severe liver dysfunction and death. The symptoms of hepatitis C virus infection include, but are not limited to: abdominal pain, loss of appetite, liver cirrhosis, autoimmune complications, liver cancer, cryoglobulinemia, anxiety, arthritis, ascites (swelling in the stomach area), blurred vision, chills, dark urine, decline in sex drive, depression, dizziness, dry skin, edema (swelling of the hands, feet & legs), excessive bleeding, excessive gas, eye or eyesight problems (blurred vision or dry eyes), fatigue, fever, flu like symptoms, gallstones, grey, yellow, white or light colored stools, headaches, hepatalgia (pain or discomfort in liver area), hot flashes, indigestion, inflammation in the joints, insomnia, irritability, itching, jaundice (yellowing of eyes and/or skin), joint pain, kidney disease, lichen planus (a skin disease), mood changes or swings, memory loss, mental confusion, menstrual problems, muscle aches, nausea, neuropathy, rashes/red spots, red palms, rheumatoid symptoms, sensitivity to heat or cold, sleep disturbances, slow healing and recovery, sensitivity to sunlight (porphyria cutanea tarda), sialadenitis (inflammation of the salivary glands), susceptibility to illness/flu, sweating, vertigo, vomiting, water retention, weakness, weight gain, weight loss.

As used herein, "autoimmune complications" of HCV infection relate to activation of an autoimmune response in a patient and are an acute episode of HCV. This response generally is directed at the liver, causing fatigue, low-grade fever and jaundice, but may also involve extrahepatic tissues, causing, among other symptoms: amenorrhea (absence of menstrual period), bloody diarrhea (due to ulcerative colitis), abdominal pain, arthritis, rashes, anemia, glomerulonephritis (a form of kidney disease), dry eyes, keratoconjunctivitis sicca, Mooren's ulcer and dry mouth.

As used herein, "cryoglobulinemia", refers generally to the condition of having the immunoglobulin, cryoglobulin, in the blood. Cryoglobulinemia is also an acute episode of HCV. At cool temperatures, these cryoglobulins turn into a gel, and may cause inflammation of the blood vessels.

Diagnosis of an acute episode of HCV can also direct treatment of the disease using specific therapeutics. As used herein, "specific therapy" for hepatitis C infection includes, but is not limited to, the administration of antiviral medications, including interferon, ribavirin and PEGinterferon.

As used herein, "sickle cell anemia" refers to an inherited disease caused by an abnormality in a hemoglobin protein, e.g., hemoglobin S (sickle hemoglobin), HbC, HbD, and HbO-Arab. The term sickle cell anemia also includes diseases such as sickle cell-b$^0$ thalassemia, hemoglobin SC disease, or sickle cell-b$^+$ thalassemia. Sickle cell anemia can be diagnosed by sequencing the DNA of a patient for the underlying mutation. Red blood cells in sickle cell anemia become disc shaped, fragile and inflexible, leading to a variety of symptoms of the disease, e.g., joint pain and other bone pain, fatigue, breathlessness, rapid heart rate, delayed growth and puberty, susceptibility to infections, ulcers on the lower legs (in adolescents and adults), jaundice, bone pain, attacks of abdominal pain, and fever.

Sickle cell anemia can become life-threatening or acute when damaged red blood cells break down (hemolytic crisis), when the spleen enlarges and traps the blood cells (splenic sequestration crisis), or when a certain type of infection causes the bone marrow to stop producing red blood cells (aplastic crisis). Repeated crises can cause damage to the kidneys, lungs, bones, eyes, and central nervous system. Blocked blood vessels and damaged organs can also cause acute painful episodes. These painful crises, which occur in almost all patients at some point in their lives, can last hours to days, affecting the bones of the back, the long bones, and the chest.

As used herein, "transplantation procedure" refers to transfer of an organ, e.g., heart, lungs, kidney, cornea, or liver, or of cells from a donor to a recipient. In preferred embodiments, the donor is a human and the recipient is a human. In some embodiments, the transplantation procedure is a bone marrow transplant, in which healthy bone marrow is transferred from a donor to a recipient who lacks functioning bone marrow or has a disease associated with blood cells, such as leukemia.

A "complication of a transplantation procedure" includes transplant rejection, graft versus host disease (GVDH), and infection and is an acute episode of a transplantation procedure. Identification of changes in complement pathway components on erythrocytes that are associated with complications of transplant procedures can lead to more effective and targeted therapeutic intervention or be used to predict the outcome of the transplantation procedure.

As used herein, the term "pregnancy" relates generally to the state of containing unborn young within the body. Normally, pregnancy progresses smoothly from conception to birth. However, pregnancy may include complications which include, but are not limited to, one or more of the following: fetal birth defects, ectopic pregnancy, bleeding, miscarriage, loss of amniotic fluid, gestational diabetes, toxoplasmosis, group B strep association, RH disease, obstetric cholestatis, high blood pressure, uterine prolapse, morning sickness, pregnancy induced hypertension, placenta previa, fetal distress, blighted ovum, hyperemesis gravidarum, dystocia, fibroids and preeclampsia. These complications are acute episodes of pregnancy that can be diagnosed, monitored or predicted be determining levels of complment pathway components on reticulocytes. The term, "preeclampsia" or "toxemia" or "pregnancy-induced hypertension", as used herein, refers to the development of swelling, elevated blood pressure, and protein in the urine during pregnancy. Symptoms of preeclampsia include, but are not limited to: edema, weight gain in excess of two pounds per week, headache, decreased urine output, nausea, vomiting, facial swelling, high blood pressure, agitation, vision changes and abdominal pain. Preeclampsia has been associated with certain autoimmune disorders including systemic lupus erythematosus (also known as "lupus" or "SLE") and anti-phospholipid syndrome (also known as "antiphospholipid syndrome" or "APS"). As used herein, the term "anti-phospholipid syndrome" or "antiphospholipid syndrome" or "APS" refers to an autoimmune disease where the body recognizes phospholipids as foreign and produces antibodies against them. APS is often associated with fetal loss during pregnancy with antiphospholipid antibodies present in about one in five women with recurrent pregnancy losses. The causes of this are unknown, but may be due to the creation of blood clots in the mother.

The causes of complications during pregnancy are often difficult to diagnose, especially those associated with autoimmune disorders, such as lupus and APS, as they often show similar symptoms. Further, complications associated with lupus pregnancies, in particular, are often difficult to differentiate from other pregnancy complications, due to the vagueness of the disease and the multiple ways the disease presents in patients. "Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F (ab)'$_2$, a dimer of Fab which itself is a light chain joined to $V_H$—$C_H1$ by a disulfide bond. The F (ab)'$_2$ may be reduced under mild conditions to break the disulfide linkage in the hinge region, thereby converting the F (ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of antibodies, e.g., recombinant, monoclonal, or polyclonal antibodies, many techniques known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

In one embodiment, the antibody is conjugated to an "effector" moiety. The effector moiety can be any number of molecules, including labeling moieties such as radioactive labels or fluorescent labels for use in diagnostic assays.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to a component of the complement pathway or to a marker of a white blood cell, polymorphic variants, alleles, orthologs, and conservatively modified variants, or splice variants, or portions thereof, can be selected to obtain only those polyclonal antibodies that are specifically immunoreactive with the component of the complement pathway or the marker of a white blood cell and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

An "antigen" is a molecule that is recognized and bound by an antibody, e.g., peptides, carbohydrates, organic molecules, or more complex molecules such as glycolipids and glycoproteins. The part of the antigen that is the target of antibody binding is an antigenic determinant and a small functional group that corresponds to a single antigenic determinant is called a hapten.

A "label" is a composition detectable by spectroscopic, photochemical, biochemical, immunochemical, or chemical means. For example, useful labels include $^{32}P$, $^{125}I$, fluorescent dyes, electron-dense reagents, enzymes (e.g., as commonly used in an ELISA), biotin, digoxigenin, or haptens and proteins for which antisera or monoclonal antibodies are available (e.g., antibody specific for a component of the complement pathway or a marker of a white blood cell can be made detectable, e.g., by incorporating a radiolabel or fluorescent label into the antibody, and used to detect component of the complement pathway or the marker of a white blood cell specifically reactive with the labeled antibody). A labeled secondary antibody can also be used to detect an antibody specific for a component of the complement pathway or a marker of a white blood cell.

The term "contact" or "contacting" is used herein interchangeably with the following: combined with, added to, mixed with, passed over, incubated with, flowed over, etc.

The term "immunoassay" is an assay that uses an antibody to specifically bind an antigen. The immunoassay is characterized by the use of specific binding properties of a particular antibody to isolate, target, and/or quantify the antigen.

In both instances, when speaking of "determination or determining" and "quantity," we mean to include both an amount or quantity of material. When more than one complement pathway component is measured, e.g., C4d and C3d "determination or determining" and "quantity," mean in addition, or alternatively, a ratio of a first complement pathway component to a second complement pathway component, e.g., a ratio of C4d to C3d.

Determination of the Level of a Complement Pathway Component on Reticulocytes

The invention involves conducting assays on blood samples obtained from patients to determine the level of a complement pathway component on reticulocytes in the sample. Assays for levels of complement pathway components, e.g., C4d levels, are disclosed in PCT/US02/28910, which is herein incorporated by reference for all purposes.

Samples of blood are obtained from the patient and are treated with EDTA (ethylenediaminetetraacetate) to inhibit complement activation. The samples are maintained at room temperature or under cold conditions. Assays are run preferably within 48 hours.

In some embodiments, FACS is used to isolate reticulocytes. The method is based on the observation that reticulocytes have a higher RNA content than more mature erythrocytes. The term "FACS" refers to fluorescence activated cell sorting, a technique used to separate cells according to their content of particular molecules of interest. The molecule of interest can be specific for a type of cell or for particular cell state. The molecule of interest can be fluorescently labeled directly by binding to a fluorescent dye, or by binding to a second molecule, which has been fluorescently labeled, e.g., an antibody or lectin that has been fluorescently labeled and that specifically binds to the molecule of interest. Thus, reticulocyte specific markers or RNA content can by used to isolate reticulocytes from other cells in a blood sample, in particular, from mature red blood cells. In a preferred embodiment, RNA is detected by staining with a fluorescent dye, and reticulocytes are separated from mature red cells on the basis of fluorescence. Fluorescent dyes for staining RNA can include thiazole orange and auramine O. In another preferred embodiment, reticulocytes are isolated or detected on the basis of binding to a transferrin receptor antibody. Methods for isolating reticulocytes and markers that can be used in FACS isolation of reticulocytes are know to those of skill and are found in Riley et al., J. Clin. Lab. Anal. 15:267-294 (2001), which is herein incorporated by reference for all purposes.

Reticulocytes can also be isolated using non-FACS methods, for example by using a reticulocyte specific cell surface marker, e.g., the transferrin receptor. Briefly, a blood sample is obtained from a patient and white blood cells are removed. The remaining blood cells are washed and then incubated with transferrin receptor antibody-coated beads, washed to remove nonbinding cells, and then displaced from the beads by addition of the autologous plasma. The technique is disclosed in Lach-Trifilieff et al., J. Immunol. 162:7549-7554 (1999), which is herein incorporated by reference for all purposes. Reticulocytes can also by isolated using nephelometry techniques.

The determination of the level of a complement pathway component may be done by a number of methods including flow cytometry, ELISA using reticulocyte lysates, radioimmunoassay, and nephelometry. In one embodiment of this invention, the determination of the level of complement component C4d is made using flow cytometric methods, with measurements taken by direct or indirect immunofluorescence using polyclonal or monoclonal antibodies specific for each of the two molecules. Antibodies to complement components, including C4d are commercially available, e.g., from Quidel Corp.

Methods to assay the level of a complement pathway component using antibodies are known to those of skill in the art. For example, development of an assay of this type for CR1 and for C4d is described in Freysdottir, et al., J. Immunol. Meth. vol. 135, 2005 (1991). That assay was a flow cytometric assay for CR1 and for protein fragments C4d and C3d on erythrocytes, and was described as enabling the identification of individuals having comparatively high or comparatively low levels of CR1.

Diagnosis or Monitoring of an Acute Episode of a Chronic Inflammatory Disease or Condition Diagnosis of a patient with an acute episode of a chronic inflammatory disease or condition is carried out by comparing the determination of a complement pathway component with a base value or range of values for the quantities of these entities typically present on the surfaces of reticulocytes in control subjects, e.g., normal individuals or individuals with the chronic inflammatory disease or condition at time when an acute inflammatory condition is not present. A demonstration of diagnosis of an acute episode of an inflammatory disease or condition is provided in Example 1. In normal individuals, C4d is present in relatively low levels on surfaces of reticulocytes of control individuals compared to individuals with SLE. When using flow cytometric measurement with indirect immunofluorescence, the median fluorescence intensity (MFI) of C4d on reticulocytes in healthy individuals ranged from 0 to 4.68, (median 1.08, SD=0.81). In contrast, individuals with SLE had a wide spectrum of reticulocyte-bound C4d (R-C4d) levels (median fluorescence intensity (MFI)=5.05; SD=8.53; range: 0 to 66.81). Reticulocyte C4d levels fluctuated significantly within individual patients with SLE, and increases in reticulocyte C4d levels were accompanied by increased disease activity.

A particular feature of the methods of this invention is the ability to monitor the activity of a patient's disease. The life span of a red blood cell is approximately 120 days, and a reticulocyte is an immature red blood cell, e.g., from about 0-2 days after leaving the bone marrow. Therefore, a particular feature of this assay or method is to indicate or reflect inflammatory disease or condition activity that is occurring or has occurred over the previous 0-2 days or at most one week. It is also possible, using this procedure, to predict the occurrence of an acute episode of a chronic inflammatory disease or condition by detecting increases in complement pathway components on surface of reticulocytes.

Kits

Kits for conducting the assays for diagnosing or monitoring or predicting disease activity are a part of the invention. Said kits will use any of the various reagents needed to perform the methods described herein. For example using the immunofluorescence assays, the kits will generally comprise a conjugate of a monoclonal antibody specific for complement pathway component with a fluorescent moiety. Polyclonal antibodies specific for the complement pathway component can also be used. The kit can also include a reagent for detection or isolation of reticulocytes, particularly for use in flow cytometric or FACS methods. The kit can also contain antibody conjugated beads for isolation of reticulocytes, e.g., anti-transferrin antibodies. The kit can also include a control level of complement pathway component or a means to determine such a control level.

Additionally, the kits will comprise such other material as may be needed in carrying out assays of this type, for example, buffers, radiolabelled antibodies, colorimeter reagents, and instructional materials etc.

The antibodies for use in these methods and kits are known. For example, anti-C4d antibodies are available from Quidel Corp. in San Diego, Calif. (#A213) and are generally described in Rogers, J., N. Cooper, et al. *PNAS* 89:10016-10020, 1992; Schwab, C. et al. *Brain Res* 707(2):196 1996; Gemmell, C. *J Biomed Mater Res* 37:474-480, 1997; and, Stoltzner, S. E., et al. *Am J Path* 156:489-499, 2000.

The determination of the complement pathway component values may alternatively be conducted using a number of standard measurement techniques such as ELISA. Instead of fluorescent labels, there may be used labels of other types, such as radioactive and calorimetric labels. If such other types of assays are to be used, the kits will comprise monoclonal or polyclonal antibodies specific for complement pathway component conjugated with appropriate labels such as radioactive iodine, avidin, biotin or enzymes such as peroxidase.

In some embodiments determinations of more than one complement pathway component on reticulocytes are made and are used to diagnose or monitor or predict acute inflammatory conditions, including acute episodes of SLE.

Automation and Computer Software

The determinations of complement pathway components on reticulocytes and the diagnostic and disease activity monitoring or predicting methods described above can be carried out manually, but often are conveniently carried out using an automated system and/or equipment, in which the blood sample is analyzed automatically to make the necessary determination or determinations, and the comparison with the base or reference value, e.g., a control level, is carried out atuomatically, using computer software appropriate to that purpose.

Thus, in one aspect, the invention comprises a method for diagnosing or monitoring an acute episode of a chronic inflammatory disease or condition in an individual comprising (a) automatically determining, in a blood sample from the individual containing reticulocytes, a complement pathway component deposited on surfaces of reticulocytes in the sample, and (b) automatically comparing said determinations with reference values for the complement pathway component, respectively, on reticulocytes.

Computer software, or computer-readable media for use in the methods, e.g., of diagnosing acute episode of SLE, of this invention include:

(1): a computer readable medium, comprising:
(a) code for receiving data corresponding to a determination of complement pathway component, e.g., C4d, deposited on surfaces of reticulocytes;
(b) code for retrieving a reference value for the complement pathway component, e.g., C4d, deposited on surfaces of reticulocytes of individuals; and
(c) code for comparing the data in (a) with the reference value of (b).

In embodiments of the invention, one or more reference values may be stored in a memory associated with a digital computer. After data corresponding to a determination of the level of a complement pathway component is obtained (e.g., from an appropriate analytical instrument), the digital computer may compare the complement pathway component data with one or more appropriate reference values. After this comparison takes place, the digital computer can automatically determine if the data corresponding to the determination of complement pathway component is associated with an acute episode of a chronic inflammatory disease or condition, e.g., SLE.

Those of skill will recognize that computer programs can be modified to analyze levels of more than one complement pathway component on reticulocytes for diagnosis of an acute inflammatory episode, including an acute SLE episode. Such analysis can also be used to predict occurrence of an acute inflammatory episode, including an acute SLE episode.

Accordingly, some embodiments of the invention may be embodied by computer code that is executed by a digital computer. The digital computer may be a micro, mini or large frame computer using any standard or specialized operating system such as a Windows™ based operating system. The code may be stored on any suitable computer readable media. Examples of computer readable media include magnetic, electronic, or optical disks, tapes, sticks, chips, etc. The code may also be written by those of ordinary skill in the art and in any suitable computer programming language including, C, C++, etc.

The following examples are provided by way of illustration only and not by way of limitation. Those of skill will readily recognize a variety of noncritical parameters which could be changed or modified to yield essentially similar results.

EXAMPLES

Example 1

Patients with SLE Have Increased Levels of C4d on the Surface of Reticulocytes

Systemic lupus erythematosus (SLE) is a disorder characterized by unpredictable multi-organ flares, i.e., an acute phase of the disease. Measurement of serum C3 and C4 and soluble complement activation products has been shown to have limited utility in monitoring the course of SLE. However, significant levels of C4-derived ligands are deposited on the surface of erythrocytes of patients with SLE. Measurement of erythrocyte c4d (E-C4d) was determined to be a useful diagnostic test for SLE and fluctuating levels of E-C4d in a given patient were found to reflect changes in disease activity.

Reticulocytes are the youngest form of erythrocytes (0-2 days old) and when emerging from the bone marrow during an active disease state, are immediately be exposed to and acquire high levels of C4-derived activation products. Therefore, examination of the levels of C4-derived activation products on the surface of reticulocytes circulating at any given time provides immediate clues to current and impending disease activity in patients with SLE. Two-color flow cytometric analyses was performed to measure C4d on reticulocytes of SLE patients (n=256), and healthy controls (n=116). The results, shown graphically in FIG. 1 and in Table 1, indicated that a wide spectrum of reticulocyte-bound C4d (R-C4d) levels was detected in SLE patients (median fluorescence intensity (MFI)=5.05; SD=53; range: 0 to 66.81), but not in patients with other AD (MFI=1.51; SD=1.35; range: 0 to 6.90) or healthy controls (MFI=1.08; SD=0.81; range: 0 to 4.68). In a cross-sectional comparison, the mean R-C4d level of SLE patients was higher than that of patients with other AD ($p<0.0001$) or that of healthy controls ($p<0.0001$).

TABLE 1

Median Fluorescence Intensity, R-C4, from SLE patients, patients with other diseases and healthy controls.

| SLE Patient # | R-C4 | Other Dis # | R-C4 | Control # | R-C4 |
|---|---|---|---|---|---|
| 1001 | 2.11 | 3002 | 0.98 | 2003 | 0.47 |
| 1002 | 3.81 | 3003 | 2.73 | 2005 | 1.97 |
| 1003 | 29.52 | 3014 | 0.31 | 2006 | 0.88 |
| 1004 | 17.76 | 3021 | 3.47 | 2007 | 2.86 |
| 1006 | 31.86 | 3022 | 1.8 | 2009 | 2.65 |
| 1007 | 2.08 | 3028 | 1.55 | 2010 | 1.52 |
| 1008 | 4.28 | 3029 | 1.97 | 2011 | 1.04 |
| 1009 | 2.32 | 3030 | 2.05 | 2013 | 0.73 |
| 1010 | 5.5 | 3031 | 6.34 | 2017 | 0.9 |
| 1011 | 2.51 | 3032 | 1.88 | 2021 | 0.15 |
| 1012 | 0.9 | 3034 | 1.26 | 2022 | 1.29 |
| 1013 | 11.58 | 3035 | 2.86 | 2025 | 0.59 |
| 1014 | 4.21 | 3036 | 1.26 | 2026 | 0.59 |
| 1015 | 9.04 | 3037 | 1.48 | 2037 | 0.66 |
| 1016 | 2.06 | 3038 | 1.36 | 2038 | 1.34 |
| 1017 | 0.7 | 3039 | 0.81 | 2039 | 1.4 |
| 1018 | 1.94 | 3040 | 1.07 | 2040 | 1.12 |
| 1021 | 0.72 | 3041 | 0.73 | 2041 | 1.11 |
| 1022 | 1.41 | 3042(13015) | 0.06 | 2042 | 1.11 |
| 1023 | 8.99 | 3043 | 0.95 | 2043 | 0.99 |
| 1027 | 2.43 | 3044 | 1.55 | 2045 | 1.43 |
| 1030 | 0.26 | 3045 | 0.83 | 2046 | 0.74 |
| 1031 | 2.93 | 3046 | 0.51 | 2047 | 1.58 |
| 1032 | 4.47 | 3047 | 0.88 | 2048 | 1.75 |
| 1034 | 6.45 | 3048 | 1.07 | 2049 | 2.62 |
| 1035 | 3.66 | 3049 | 5.33 | 2050 | 0.76 |
| 1036 | 44.39 | 3050 | −0.03 | 2051 | 0.64 |
| 1037 | 1.25 | 3051 | 2.42 | 2052 | 1.67 |
| 1038 | 27.21 | 3052 | 1.07 | 2053 | 4.68 |
| 1039 | 3.34 | 3053 | 0.81 | 2054 | 1.45 |
| 1041 | 1.86 | 3054 | 3.13 | 2055 | 1.01 |
| 1042 | 6.72 | 3055 | 2.08 | 2056 | 1.91 |
| 1043 | −0.38 | 3056 | 1.06 | 2057 | 1.62 |
| 1044 | 2.77 | 3057 | 0.96 | 2058 | 2.24 |
| 1045 | 3.58 | 3058 | 1.72 | 2059 | 1.51 |
| 1047 | 2.32 | 3059 | 1.8 | 2060 | 1.41 |
| 1048 | 3.19 | 3060 | 4.59 | 2061 | 1.49 |
| 1050 | 15.11 | 3061 | 3.42 | 2062 | 1.09 |
| 1052 | 10.65 | 3062 | 0.59 | 2063 | 3.23 |
| 1053 | 24.9 | 3063 | 1.37 | 2064 | 0.36 |
| 1054 | 40.66 | 3064 | 1.44 | 2065 | 0.76 |
| 1055 | 9.47 | 3065 | 1.44 | 2066 | 3.32 |
| 1056 | 1.79 | 3066 | 1.72 | 2067 | 2.81 |
| 1057 | 3.81 | 3067 | 0.96 | 2068 | 1.74 |
| 1059 | 17.84 | 4001 | 0.77 | 2069 | 0.81 |
| 1060 | 0.84 | 4002 | 0.15 | 2070 | 0.15 |
| 1061 | 1.46 | 4006 | 0.29 | 2071 | 0.66 |
| 1062 | 5.28 | 4007 | 0.92 | 2072 | 0.21 |
| 1063 | 3.74 | 4011 | 0.18 | 2073 | −0.31 |
| 1064 | 3.61 | 4013 | 0.35 | 2074 | 0.37 |
| 1065 | 3.53 | 4017 | 1.53 | 2075 | 1.34 |
| 1066 | 36.64 | 4020 | 2.52 | 2076 | 0.28 |
| 1067(1114) | 3.04 | 4021 | 3.36 | 2077 | 0.73 |
| 1071 | 0.78 | 4025 | 5.7 | 2078 | 0.39 |
| 1072 | 3.39 | 4026 | 2.01 | 2079 | 1.72 |
| 1073 | 3.18 | 4027 | 0.62 | 2080 | 0.82 |
| 1074 | 1.05 | 4028 | 1.98 | 2081 | −1.24 |
| 1075 | 2.5 | 4030 | 2.01 | 2082 | 1.11 |
| 1078 | 7.72 | 4033 | 0.18 | 2083 | 2.17 |
| 1079 | 2.98 | 4034 | 1.9 | 2084 | 0.93 |
| 1080 | 4.16 | 4035 | 0.2 | 2085 | 1.21 |
| 1082 | 4 | 4036(13053) | 0.56 | 2086 | 2.01 |
| 1083 | 3.22 | 4037 | 0.63 | 2087 | 0.44 |
| 1084 | 6.5 | 4038 | 0.65 | 2088 | 0.44 |
| 1085 | 1.04 | 4039 | 1.45 | 2089 | −0.05 |
| 1086 | −0.2 | 4040 | 0.92 | 2090 | 1.92 |
| 1089 | 0.84 | 4041 | 1.93 | 2091 | 1.79 |
| 1090 | 25.02 | 4042 | 0.15 | 2092 | 0.99 |
| 1091 | 1.63 | 4043 | 0.85 | 2093 | 2.1 |
| 1092 | 0.86 | 4044 | 2.12 | 2094 | 0.34 |
| 1093 | 5.55 | 4045 | 1.87 | 2095 | 1.1 |
| 1094 | 6.41 | 4046 | 7.75 | 2096 | 2.92 |
| 1095 | 7.67 | 4047 | 1.3 | 2097 | 1.47 |
| 1096 | 9.62 | 4048 | 2.08 | 2098 | 0.73 |
| 1097 | 41.23 | 5001 | 1.58 | 2099 | 1.13 |
| 1098 | −0.21 | 5004 | 0.37 | 2100 | 1.53 |
| 1099 | −0.11 | 5005 | 0.47 | 2101 | 1.06 |
| 1100 | 3.16 | 5006 | 1.84 | 2102 | 0.73 |
| 1101 | 66.81 | 5008 | 4.11 | 2103 | −0.09 |
| 1102 | 29.17 | 5009 | 2.83 | 2104 | 0.72 |
| 1103 | 1.75 | 5010 | 0.37 | 2105 | 0.55 |
| 1104 | 1.5 | 5011 | 1.64 | 2106 | 0.26 |
| 1105 | 14.77 | 5012 | 1.21 | 2107 | 0.83 |
| 1106 | 1.9 | 5013 | 2.68 | 2108 | 0.38 |
| 1107 | 1.29 | 5014 | 1.72 | 2109 | 0.37 |
| 1108 | 1.37 | 5015 | 1.21 | 2110 | 0.25 |
| 1109 | 1.6 | 5016 | 0.66 | 2111 | 0.44 |
| 1110 | 10.96 | 5017 | 3.6 | 2112 | 0.37 |
| 1111 | 1.07 | 5018 | 8.45 | 2113 | 0.4 |
| 1115 | 0.93 | 5019 | 17.6 | 2114 | 1.26 |
| 1116 | 1.51 | 6001 | 2.47 | 2115 | 0.44 |
| 1117 | −0.87 | 6002 | 1.71 | 2116 | 0.75 |
| 1118 | 16.92 | 6003 | 1.72 | 2117 | 0.57 |
| 1119 | 0.42 | 6004 | 1.93 | 2118 | 0.71 |
| 1120 | 0.01 | 6005 | 0.77 | 2119 | 0.54 |
| 1121 | 16.92 | 6008 | 1.89 | 2120 | 0.48 |
| 1122 | 0.53 | 6009 | 0.56 | 2121 | 0.26 |
| 1123 | 0.55 | 6011 | 0.75 | 2122 | 0.92 |
| 1124 | 20.73 | 6012 | 0.91 | 2123 | 0.85 |
| 1125 | 8.97 | 6013 | 1.66 | 2124 | 0.24 |
| 1126 | 3.58 | 6014 | 1.84 | 2125 | 0.51 |
| 1127 | 2.1 | 6015 | 3.29 | 2126 | 0.45 |
| 1128 | 1.34 | 6017 | 0.33 | 2127 | 1.34 |
| 1129 | 4.84 | 6018 | 2.16 | 2128 | 1.31 |
| 1130 | 5.76 | 6019 | −0.31 | 2129 | 1.31 |
| 1131 | 2.58 | 6020 | 0.5 | 2130 | 1.7 |
| 1132 | 18.36 | 6021 | 0.54 | 2131 | 1.17 |
| 1133 | 2.79 | 6022 | 0.42 | 2132 | 1.5 |
| 1136 | 9.65 | 6023 | 0.77 | 2133 | 1.28 |
| 1137 | 7.08 | 6024 | 10.55 | 2134 | 1.07 |
| 1138 | 0.97 | 6025 | 1.14 | 2135 | 0.84 |
| 1139 | 1.26 | 6026 | 1.06 | 2136 | 0.76 |
| 1140 | 1.32 | 6027 | 1.7 | 2137 | 1.5 |
| 1141 | 1.03 | 6028 | 0.65 | 2139 | 0.56 |
| 1142 | 3.79 | 6029 | 2.22 | 2141 | 0.81 |
| 1143 | 0.21 | 6030 | 3.21 | 2142 | 0.67 |
| 1145 | 1.17 | 6031 | 1.03 | 2143 | 0.76 |
| 1146 | 3.05 | 6032 | 1.43 | 2144 | 0.54 |
| 1147 | 5.74 | 6033 | 0.35 | 2145 | 0.36 |
| 1148 | 8.46 | 6034 | 1.19 | 2146 | 0.03 |
| 1149 | 1.27 | 6035 | 1.25 | 2147 | 0.44 |
| 1150 | 9.03 | 6036 | 0.73 | 2029 | 0.67 |
| 1152 | 5.46 | 7001 | 1.2 | 2148 | 2.01 |
| 1153 | 10.17 | 7002 | 0.61 | 2149 | 0.55 |
| 1154 | 3.69 | 7003 | 0.33 | 2154 | 0.84 |
| 1155 | 1.73 | 7004 | 0.61 | 2156 | 1.15 |
| 1156 | 1.25 | 7005 | 0.41 | 2152 | 0.32 |
| 1157 | 5.74 | 8013 | 0 | 2155 | 0.56 |
| 1159 | 2.29 | 8021 | 1.56 | 2153 | 0.65 |
| 1161 | 1.19 | 8035 | 1.82 | 2150 | 0.99 |
| 1162 | 1.03 | 10001 | 6.9 | 2151 | −0.02 |
| 1163 | 3.14 | 10002 | 1.02 | 2157 | 0.98 |
| 1164 | 2.56 | 10003 | 0.1 | 2158 | 1.29 |
| 1165 | 1.12 | 15002 | 1.01 | 2160 | 1.41 |
| 1166 | 1.1 | 15003 | 1.9 | 2159 | 0.65 |
| 1167 | 2.29 | 15005 | 0.79 | 2161 | 1.09 |
| 1168 | 2.44 | 15006 | 0.46 | 2162 | −0.08 |
| 1169 | 0.16 | 17002 | 4.72 | 2163 | 1.65 |
| 1170 | 2.19 | 17003 | 2.02 | 2164 | 1.4 |
| 1171 | 1.94 | 17004 | 0.97 | 2165 | 0.98 |
| 1172 | 2.51 | 18001 | 0.91 | 2166 | 0.37 |
| 1173 | 3.48 | 18002 | 2.77 | 2167 | 0.55 |
| 1174 | 0.7 | 19001 | 0.31 | 2168 | 0.47 |
| 1176 | 1.92 | 13001 | 3.87 | 2032(2169) | 0.89 |
| 1177 | 1.02 | 13003 | 0.73 | 2170 | 1.4 |
| 1178 | 2.97 | 13007 | 1.37 | 2171 | 0.57 |
| 1179 | 0.52 | 13008 | 1.45 | 2172 | 1.25 |
| 1180 | 1.63 | 13010 | 2.51 | 2173 | 0.58 |

TABLE 1-continued

Median Fluorescence Intensity, R-C4, from SLE patients, patients with other diseases and healthy controls.

| SLE Patient # | R-C4 | Other Dis # | R-C4 | Control # | R-C4 |
|---|---|---|---|---|---|
| 1181 | 2.44 | 13011 | 0.95 | 2174 | 1.99 |
| 1182 | 4.86 | 13012 | 0.68 | 2175 | 0.16 |
| 1183 | 8.72 | 13015 | 0.06 | 2176 | 1.44 |
| 1184 | 0.18 | 13016 | 3.96 | 2177 | 1.07 |
| 1185(13025) | 3.61 | 13017 | 1.82 | 2178 | 1.38 |
| 1186 | 2.93 | 13018 | 1.34 | 2179 | 0.78 |
| 1187 | 1.06 | 13019 | 3.36 | 2180 | 0.71 |
| 1188 | 3.27 | 13020 | 0.36 | 2181 | 0.83 |
| 1189(13037) | 10.76 | 13021(1144) | 1.56 | 2182 | 0.09 |
| 1193 | 1.21 | 13022 | 0.6 | 2183 | 0.63 |
| 1194 | 17.05 | 13023 | 1.92 | 2184 | 1.53 |
| 1195 | 1.56 | 13024(1151) | 1.55 | | |
| 1196 | 1.32 | 13026 | 4.36 | | |
| 1197 | 1.92 | 13027 | 0.63 | | |
| 1198 | 1.8 | 13028 | 1.47 | | |
| 1199 | 1.49 | 13029 | 1.05 | | |
| 1200 | 1.98 | 13030(2044) | 0.43 | | |
| 1201 | 1.47 | 13031 | 4.35 | | |
| 1202 | 1.97 | 13032 | 1.51 | | |
| 1203 | 0.8 | 13033 | 1.43 | | |
| 1204 | 6.34 | 13034 | 0.77 | | |
| 1205 | −0.21 | 13035 | 1.29 | | |
| 1206 | 1.18 | 13036 | 2.18 | | |
| 1207 | 0.9 | 13038 | 0.58 | | |
| 1208 | 2.6 | 13039 | 8.96 | | |
| 1209 | 22.72 | 13040 | 1.03 | | |
| 1210 | 9.66 | 13041(1160) | 0.91 | | |
| 1211 | 0.75 | 13042 | 21 | | |
| 1212 | 2.73 | 13043 | 0.36 | | |
| 1213 | 5.15 | 13044(1190) | 1.18 | | |
| 1214 | 1.97 | 13045 | 1.37 | | |
| 1215 | 3.07 | 13046(1175) | 1.29 | | |
| 1216 | 0.97 | 13047 | 0.53 | | |
| 1217 | 1.9 | 13048 | 0.6 | | |
| 1218 | 31.39 | 13050 | 0.53 | | |
| 1219 | 1.27 | 13051 | 0.19 | | |
| 1220 | 0.08 | 13054 | 0.31 | | |
| 1221 | 1.62 | 13056 | 0.77 | | |
| 1222 | 3.23 | 13057 | 2.57 | | |
| 1223 | 1.2 | 13058 | 1.96 | | |
| 1224 | 2.46 | 13059 | 1.45 | | |
| 1225 | 1.22 | 13060 | 0.98 | | |
| 1226 | 0.32 | 13061 | 2.67 | | |
| 1227 | 0.18 | 13062 | 0.39 | | |
| 1228 | 0.44 | 13065 | 0.27 | | |
| 1229 | 1.26 | 13066 | 0.3 | | |
| 1230 | 2.71 | 13067 | 38.3 | | |
| 1231 | 0.79 | 13069 | 1.28 | | |
| 1232 | 2.64 | 13070 | 1.77 | | |
| 1233 | 0.88 | 13071 | 2.54 | | |
| 1234 | 0.96 | 13074 | 1.98 | | |
| 1235 | 5.59 | 13075 | 2.56 | | |
| 1236 | 2.71 | 13076 | 1.93 | | |
| 1237 | 0.82 | 13077 | 1.2 | | |
| 1238 | 0.53 | 13078 | 1.15 | | |
| 1239 | 5.07 | 13079 | 3.85 | | |
| 1240 | 0.24 | 13080 | 1.17 | | |
| 1241 | 0.4 | 13081 | 1.77 | | |
| 1242 | 0.54 | 13082 | 9.84 | | |
| 1243 | 2.13 | 13084 | 3.51 | | |
| 1244 | 8.03 | 13085 | 0.67 | | |
| 1245 | 9.55 | 13086 | 3.83 | | |
| 1246 | 0.34 | 13087(1294) | 2.22 | | |
| 1247 | 0.56 | 13088 | 7.88 | | |
| 1248 | 0.41 | 13089 | 0.38 | | |
| 1249 | 2.46 | 13090 | 2.51 | | |
| 1250(13052) | 0.5 | 13091 | 0.13 | | |
| 1251 | 3.29 | | | | |
| 1252 | 1.26 | | | | |
| 1253 | 4.65 | | | | |
| 1254 | 0.99 | | | | |
| 1255 | 2.26 | | | | |
| 1256 | 0.39 | | | | |
| 1257 | 7.2 | | | | |
| 1258(13055) | 15.81 | | | | |
| 1259 | 0.87 | | | | |
| 1260 | −0.52 | | | | |
| 1261 | 1.2 | | | | |
| 1262 | 1.43 | | | | |
| 1263 | 2.58 | | | | |
| 1264 | 1.79 | | | | |
| 1266 | 11.86 | | | | |
| 1267 | 0.9 | | | | |
| 1268 | 0.51 | | | | |
| 1269 | 2.69 | | | | |
| 1270 | 4.12 | | | | |
| 1271 | 5.09 | | | | |
| 1272(13063) | 0.75 | | | | |
| 1273 | 0.36 | | | | |
| 1274(13064) | 4.88 | | | | |
| 1275(13068) | 1.17 | | | | |
| 1276 | 0.92 | | | | |
| 1277 | 1.18 | | | | |
| 1278 | 3.08 | | | | |
| 1280 | 0.47 | | | | |
| 1281 | 0.57 | | | | |
| 1282 | 13.38 | | | | |
| 1283 | 5.31 | | | | |
| 1284 | 1.48 | | | | |
| 1285 | 0.83 | | | | |
| 1286 | 54.27 | | | | |
| 1287 | 0.99 | | | | |
| 1288 | 1.33 | | | | |
| 1289 | 2.01 | | | | |
| 1290 | 6.56 | | | | |
| 1291 | 1.83 | | | | |
| 1292 | 5.51 | | | | |
| 1293 | 1.01 | | | | |
| 1295 | 1.54 | | | | |
| 1296 | 4.14 | | | | |
| 1297 | 2.31 | | | | |
| 1298 | 1.8 | | | | |
| 1299 | 0.41 | | | | |
| 1300 | 0.88 | | | | |
| 1302(13073) | 0.91 | | | | |
| 1303 | 1.58 | | | | |
| 1304 | 2.25 | | | | |
| 1305 | 1.74 | | | | |
| 1306 | 4.15 | | | | |
| 1307 | 1.77 | | | | |
| 1308 | 3.65 | | | | |
| 1309 | 2.4 | | | | |
| 1310(13049) | 1.5 | | | | |
| 1311 | 13.09 | | | | |
| 1312 | 3.18 | | | | |
| 1313 | 7.28 | | | | |
| 1315 | 9.55 | | | | |
| 1316 | 10.15 | | | | |
| 1317 | 1.59 | | | | |
| 1318 | 7.1 | | | | |

Figure 2:
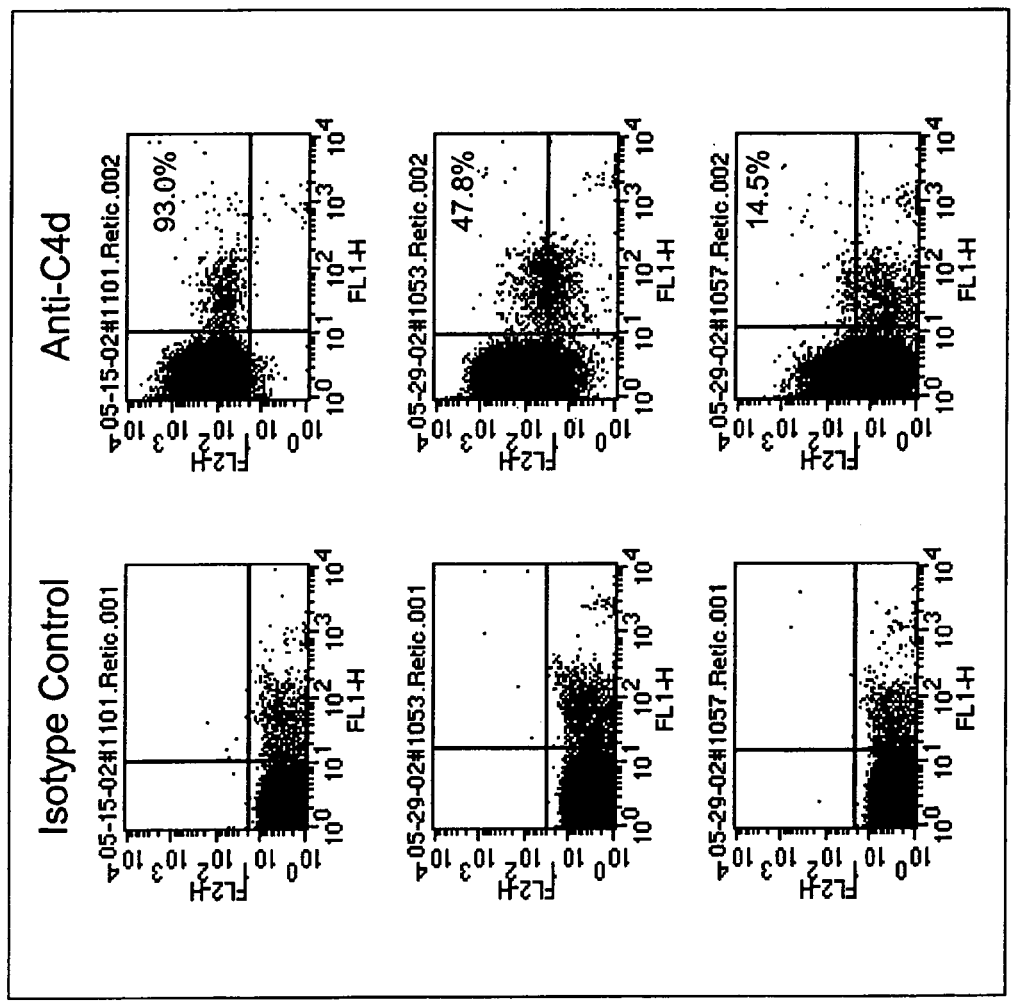
FIG. 2 provides two color flow cytometry data from each of three individual SLE patients. C4d levels are shown in the right panels, while matched isotype controls are shown in the left panels. Two color flow cytometry was performed using a labeled anti-C4d antibody (Y-axis) and a labeled anti-transferrin receptor antibody (X-axis). C4d positive reticulocytes are shown in the upper right quadrant of the panels. Results from three SLE patients are shown. 93%, 47.8%, and 14.5% of reticulocytes exhibited C4d staining. The control antibodies do not bind reticulocytes, indicating the C4d antibody binding is specific.

FIG. 2 provides examples of FACS data from individual SLE patients. C4d levels are shown in the left panels, while matched isotype controls are shown in the right panels. Red blood cells were pelleted, washed with PBSB, and aliquotted for anti-C4d or control antibody staining. Two-color flow cytometric analyses was performed to measure C4d on reticulocytes of SLE patients. Monoclonal antibodies (mAb) were added to red blood cells at a concentration of 10 μg/ml. An RNA binding dye was added to distinguish reticulocytes from erythrocytes. The cells were incubated for 20 min at 4° C., and washed with cold PBSB+0.2% sodium azide. A secondary antibody, goat anti-mouse IgG conjugated to fluorescein isothiocyanate (FITC) from Jackson Immunoresearch Laboratories (# 115-096-062) was added to cells at a concentration of 10 μg/ml. Cells were incubated and washed, resuspended in PBSB+0.2% sodium azide, and analyzed by flow cytometry using a FACSCalibur (Becton Dickinson Immunocytometry Systems, San Jose, Calif.). Nonspecific binding of immunoglobulins to cells was determined by performing identical assays in parallel using the isotype control antibody MOPC21 (obtained from ATCC). Anti-C4d binding to reticulocytes is shown in the upper right quadrant of the panel. Results from three SLE patients are shown and have 93%, 47.8%, and 14.5% C4d staining of reticulocytes. The controls do not show antibody binding to reticulocytes, indicating the C4d antibody binding is specific.

The R-C4 levels were compared to other methods for diagnosing SLE and results are shown in Table 2. Two of the most commonly used methods are the Systemic Lupus Disease Activity Index (SLEDAI) (Bombardier, et al. *Arth Rheum* 35: 630-40 (1992)), and the Systemic Lupus Activity Measure (SLAM) (Liang, et al. *Arth Rheum* 32: 1107-18 (1989)). The SLEDAI includes 24 items representing 9 organ systems. The variables are obtained by history, physical examination and laboratory assessment. Each item is weighted from 1 to 8 based on the significance of the organ involved. For example, mouth ulcers are scored as 2, while seizures are scored as 8. The laboratory parameters that are included in the SLEDAI include white blood cell count, platelet count, urinalysis, serum C3, C4 and anti-dsDNA. The total maximum score is 105. The SLAM includes 32 items representing 11 organ systems. The items are scored not only as present/absent, but graded on a scale of 1 to 3 based on severity. The total possible score for the SLAM is 86. Both the SLEDAI and the SLAM have been shown to be valid, reliable, and sensitive to change over time (Liang, et al.), and are widely used in research protocols and clinical trials. These indices are particularly useful for examining the value of newly proposed serologic or inflammatory markers of disease activity in SLE.

TABLE 2

R-C4 and SLE Disease Activity

| R-C4 Level | SLEDAI | p value | SLAM | p value |
|---|---|---|---|---|
| 1st quartile (<1.1) | 1.34 | | 4.56 | |
| 2nd quartile (1.1-2.2) | 2.51 | 0.030 | 5.05 | N.S. |
| 3rd quartile (2.2-4.5) | 2.90 | 0.00003 | 6.02 | 0.06 |
| 4th quartile (>4.5) | 4.32 | 0.00003 | 6.93 | 0.002 |

Statistical analysis of 164 SLE patients showed that the level of R-C4d correlated with clinical disease activity as measured using SLEDAI and SLAM. See, e.g., Table 2. Specifically, patients with R-C4d>4.5 (the highest quartile), compared to those with R-C4d<1.1 (the lowest quartile), had significantly higher SLEDAI (p=0.00003) and SLAM (p=0.002) scores. Thus, reticulocytes bearing C4-derived ligands serve as "instant messengers" of disease activity in SLE and can predict impending disease flares.

Example 2

C4d Levels on Reticulocytes can Predict Disease Flares

Prospective analyses also indicated that R-C4d levels in healthy controls are remarkably stable over time, while R-C4d levels fluctuated significantly within individual patients with SLE. Moreover, increases in R-C4d were accompanied by increased disease activity.

Figure 3:
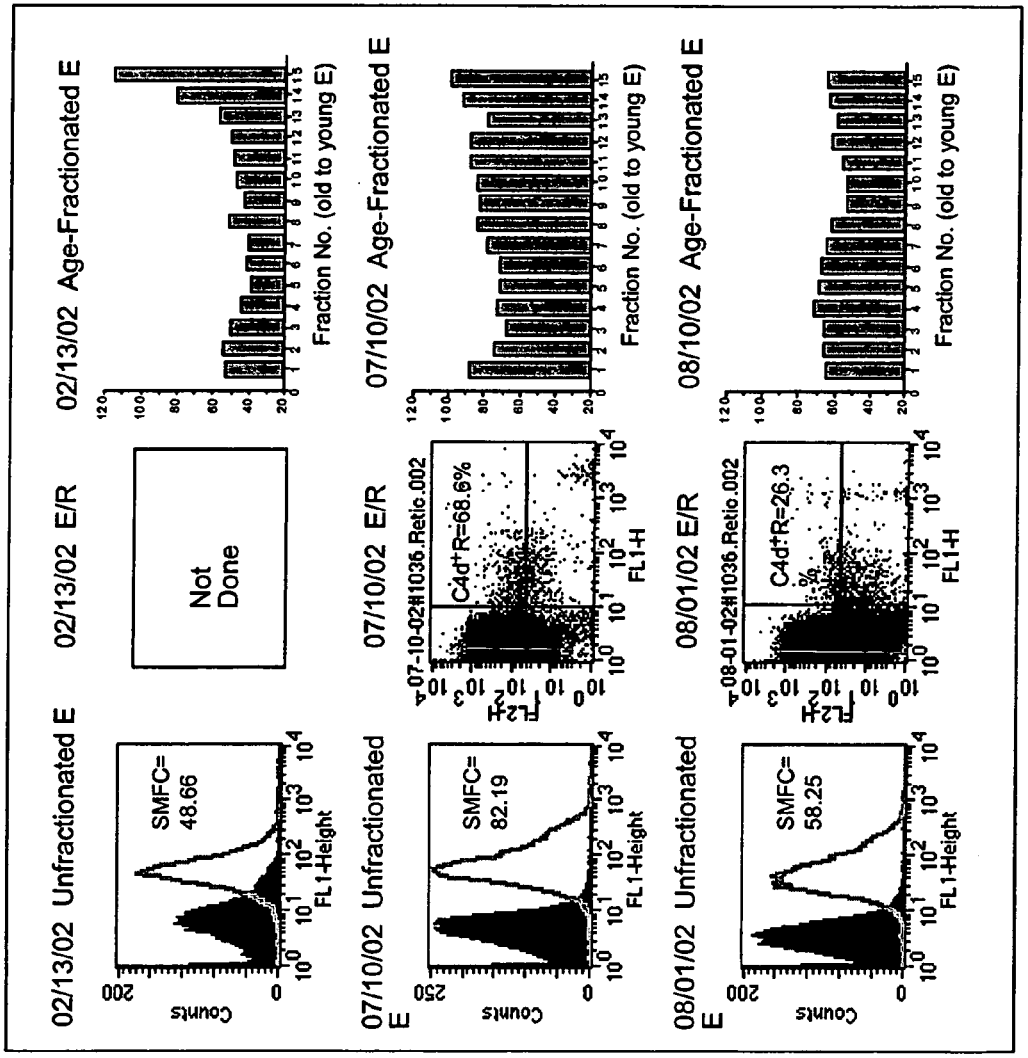
FIG. 3 provides data showing C4d levels on reticulocytes from an SLE patient at three time points: February 2002 (top row), July 2002 (middle row), and August 2002 (bottom row). C4d staining on unfractionated red blood cells, e.g., erythrocytes and reticulocytes, is shown in the left column. The middle column shows two color flow cytometry using a labeled anti-Cd4 antibody (Y-axis) and a labeled anti transferrin receptor antibody (X-axis) at different time points. C4d positive reticulocytes are shown in the upper right quadrant of the panels. The right column shows a comparison of C4d levels on erythrocytes and reticulocytes at different time points. Erythrocytes and reticulocytes were separated by density gradient centrifugation. The oldest cells elute beginning in fraction 1. Reticulocytes are found with the youngest cells eluting in fraction 15. The vertical axis shows C4d levels on the surface of the cells.

Patient DC is a 50-year-old Caucasian woman, diagnosed with SLE in 1976. Her disease has been manifested by arthritis, malar rash, fevers, pleurisy, leukopenia, thrombocytopenia, +ANA, dsDNA, SSA, SSB, Smith and persistently low levels of serum C4. On Feb. 13, 2002, she presented to the office complaining of recent onset of fatigue. She had no other symptoms and her physical examination was normal. Her serum C3 was normal and her serum C4 was low, but not significantly different from previous values. Although she appeared well, it was unclear whether her increasing fatigue was due to a viral infection, or an SLE flare. Her routine laboratory parameters were unhelpful in making this distinction. She also had a high level of C4d on the youngest fractions of her RBCs suggesting current complement activation and a possible SLE flare. See, e.g., FIG. 3. Two months later, the patient called the office complaining of severe pain and swelling of her joints with worsening fatigue and malaise, symptoms consistent with an SLE flare. Despite treatment with anti-inflammatory agents, this persisted until her visit on Jul. 10, 2002. At this visit, 68% of her reticulocytes had C4d present on the surface and all fractions of her red blood cells had high levels of C4d, indicating ongoing and previous (past 120 days) activity of her lupus. With institution of more aggressive therapy, she responded with marked improvement in her joint pain and fatigue. By Aug. 1, 2002, she was feeling well and only 26% of her reticulocytes had surface C4d. This case illustrates how reticulocytes can serve as instant messengers of lupus disease activity or for real time diagnosis of inflammatory activity.

Example 3

Correlation Between R-C4d Levels and SLE Disease Activity a Large Scale Study

Methods

Study Participants

All study participants were 18 years of age or older and provided written informed consent. No one was excluded based on gender or ethnicity. The University of Pittsburgh Institutional Review Board approved this study.

SLE Patients: Consecutive patients with SLE who met the 1982 (Tan E M et al., *Arthritis Rheum,* 25:1271-1277 (1982)) or 1997 (Hochberg M C, *Arthritis Rheum,* 40:1725 (1997)) American College of Rheumatology (ACR) revised criteria were recruited for this study during routine visits to the University of Pittsburgh Lupus Diagnostic and Treatment Center. Patients who were pregnant were excluded. As part of their routine care, all patients underwent a history and physical examination by one physician (SM or AK), who was blinded to the reticulocyte/erythrocyte-bound complement results. Disease activity was assessed at the time of the visit using the Systemic Lupus Activity Measure (SLAM) (Liang M H et al., *Arthritis Rheum,* 32:1107-1118 (1989)) and the Safety of Estrogens in Lupus Erythematosus National Assessment (SELENA) version of the Systemic Lupus Erythematosus Disease Activity Index (SLEDAI) (Bombardier C, et al., *Arthritis Rheum,* 35:630-640 (1992)).

Patients with Other Diseases: Randomly selected patients with 11 other rheumatic, inflammatory/autoimmune, or hematologic diseases, including scleroderma (n=43), myositis (n=30), Sjogren's Syndrome (n=16), rheumatoid arthritis (n=32), Wegener's granulomatosis (n=5), hepatitis C (n=3), vasculitis (n=2), primary Raynaud's phenomenon (n=4), hemophilia (n=1), psoriatic arthritis (n=2), and antiphospholipid syndrome (n=1), were recruited. The diagnoses were confirmed by their treating subspecialist physicians from various outpatient facilities at the University of Pittsburgh Medical Center.

Healthy Controls: Healthy controls were recruited through local advertisements posted on the University of Pittsburgh campus. To confirm their healthy status, participants completed a brief questionnaire querying obvious medical conditions.

Flow Cytometric Characterization of Reticulocytes and Erythrocytes

A 3-ml sample of blood was collected for each study participant at the time of the visit in VACUTAINER® tubes containing EDTA as an anticoagulant (Becton Dickinson, Franklin Lakes, N.J.), and used for experiments on the same day that it was collected. Whole blood cells were washed with phosphate buffered saline (PBS), diluted in PBS, and aliquotted for indirect immunofluorescence staining. Mouse monoclonal antibody specific for human C4d (reactive with C4d-containing fragments of C4; Quidel, San Diego, Calif.) or the isotype-matched control MOPC21 was added to cell suspensions at a concentration of 10 µg/ml. Phycoerythrin (PE)-conjugated goat anti-mouse IgG F(ab')$_2$ (Cappel) was used at a concentration of 10 µg/ml. Following antibody staining, cell suspensions were incubated with thiazole orange (ReticCount™ reagent; Becton Dickinson) to identify reticulocytes or with PBS as the vehicle control. Stained cells were analyzed by flow cytometry using a FACSCalibur flow cytometer and CellQuest software (both from Becton Dickinson Immunocytometry Systems, San Jose, Calif.). Erythrocytes were electronically gated based on forward and side scatter properties. Reticulocytes were electronically gated based on forward scatter property and positive staining with ReticCount™. Levels of C4d on the surface of reticulocytes or erythrocytes were expressed as specific median fluorescence intensity (C4d-specific median fluorescence minus the isotype control median fluorescence intensity; SMFI).

Statistical Analysis

Descriptive statistics, including means, medians, standard deviations, and ranges were computed for continuous data, and frequency distributions were determined for categorical variables. Differences in R-C4d and E-C4d levels of the three groups of study participants (patients with SLE, patients with other diseases, and healthy controls) were compared by Kruskal-Wallis test, followed by Wilcoxon rank sum tests to determine statistical significance of the differences between each of the paired study groups. Spearman Rank Correlations were used to determine the association between R-C4d and EC4-d with disease activity measured by the SLAM and SELENA-SLEDAI. Wilcoxon rank sum test was used to analyze significance of differences in SLAM or SELENA-SLEDAI scores between the first quartile group and other quartile groups of SLE patients with different R-C4d and E-C4d levels. Chi-square test for trend was used to evaluate associations between quartiles of R-C4d levels and presence of specific clinical and serologic manifestations of SLE. The statistical significance of the various tests was assessed with 2-sided hypothesis testing using Intercooled STATA 7.0 for Windows (College Station, Tex.). Differences at the p<0.05 level were considered significant.

Results

Characteristics of Study Participants

The study population consisted of 156 patients with SLE, 159 healthy controls, and 140 patients with other immune-mediated, inflammatory or hematologic diseases. The SLE participants had a mean age of 43.78+/−12.18 years, were 82.7% Caucasian, and 95.5% female. Additional demographic and clinical features of the patients with SLE are shown in Table 3. The cohort included patients with both new onset as well as longstanding disease, represented a broad range of disease activity as reflected in the SLAM and SELENA-SLEDAI scores, and had a wide spectrum of organ involvement. The healthy control participants had a mean age of 43.55+/−13.45 years, were 85% Caucasian, and 91% female. The study participants in the other diseases group had a mean age of 52.20+/−13.81 years, were 93% Caucasian, and 79.6% female.

TABLE 3

Clinical characteristics of 156 patients with systemic lupus erythematosus

| Characteristic | Patients with SLE (n = 156) |
|---|---|
| Age[a] (yr) | 43.78 +/− 12.18 (18-80) |
| Race (% Caucasian) | 82.7 |
| Sex (% female) | 95.5 |
| Disease duration[a] (yr) | 12.21 +/− 9.49 (0.01-47.06) |
| Malar rash[b] (%) | 53.2 |
| Discoid rash[b] (%) | 14.1 |
| Photosensitivity[b] (%) | 52.6 |
| Oral ulcers[b] (%) | 55.8 |
| Arthritis[b] (%) | 89.1 |
| Serositis[b] (%) | 49.4 |
| Renal disease[b] (%) | 25.8 |
| Neurological disease (%) | 7.7 |
| Hematological manifestations[b] (%) | 57.7 |
| Anemia (%) | 14.1 |
| Leukopenia (%) | 42.3 |
| Thrombocytopenia (%) | 20.5 |
| Immunological tests[b] (%) | 80.6 |
| Anti Smith (%) (n = 154) | 13.6 |
| Antiphospholipid antibodies (%) (n = 154) | 44.8 |
| Antinuclear antibodies (%) | 96.2 |
| SS-A, SS-B, rheumatoid factor, etc. (%) (n = 141) | 36.6 |
| Anti dsDNA[b,c] (%) | 69.0[b]; 39.5[c] |
| Raynaud's phenomenon[b] (%) | 43.2 |
| SLAM[a,d,e] | 5.79 +/− 3.75 (0-20) |
| SELENA-SLEDAI[a,d,e] | 2.82 +/− 2.91 (0-20) |
| Serum C3 (% below normal)[c] | 39.4 |
| Serum C4 (% below normal)[c] | 51.0 |
| Erythrocyte sedimentation rate[a] (mm/hr; n = 151) | 21.10 +/− 19.80 (0-117) |

Figure 4A:
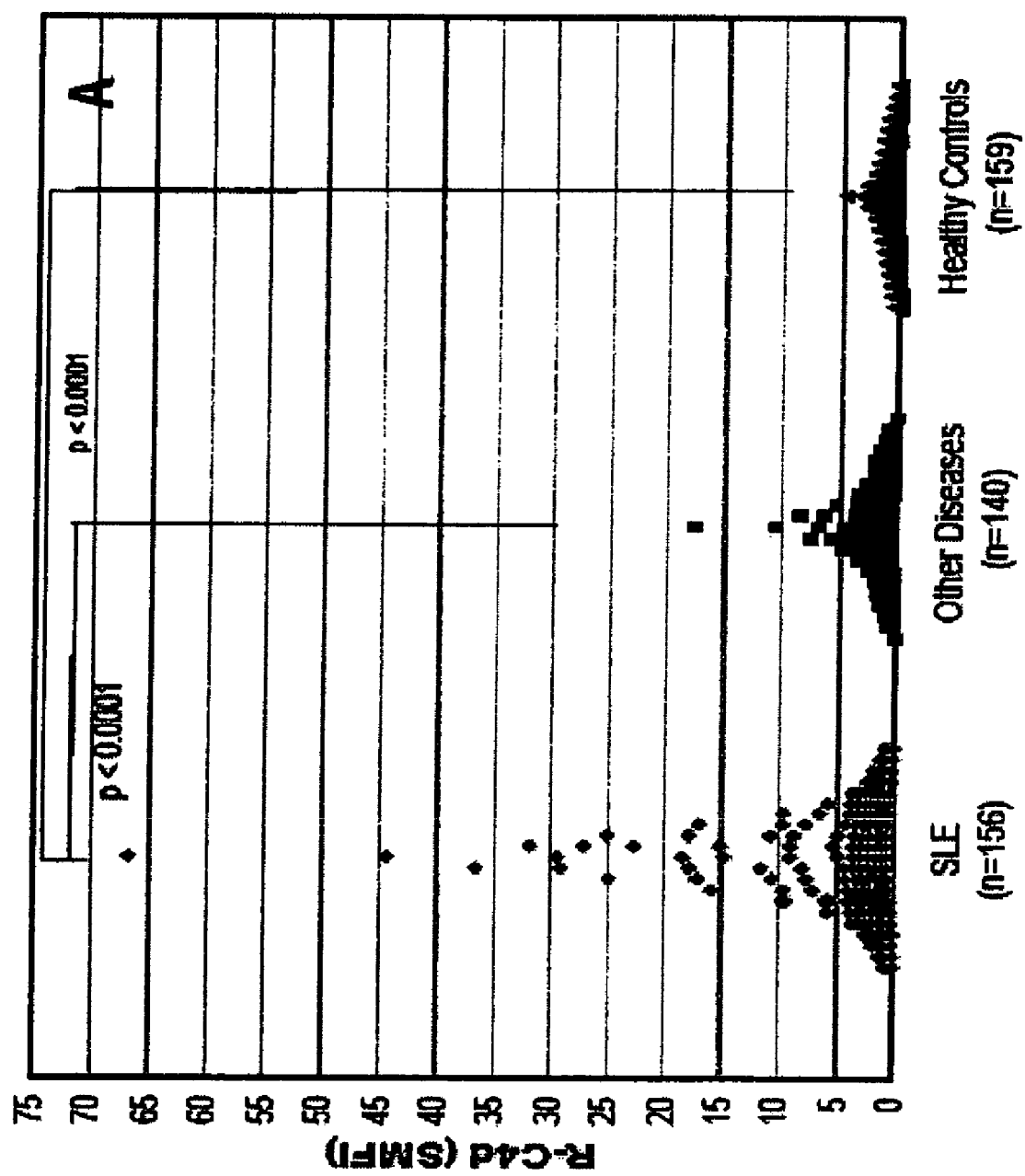
FIG. 4A-D demonstrates that reticulocyte-C4d levels are significantly elevated in patients with SLE and fluctuate over time. (A) Reticulocytes from patients with SLE have significantly higher levels of C4d than those from patients with other diseases or healthy controls. Shown on the Y-axis is the C4d-specific median fluorescence intensity for reticulocytes from 156 patients with SLE, 140 patients with other diseases, and 159 healthy controls. (B) R-C4d levels remain stable in healthy controls and patients with other diseases over time. Shown are R-C4d levels of 7 healthy controls and 16 patients with non-SLE autoimmune diseases (1 scleroderma, 7 inflammatory myopathies, 1 Sjorgren's syndrome, 6 rheumatoid arthritis, and 1 antiphospholipid antibody syndrome) examined at 3 or 4 different study visits. (C and D) R-C4d levels fluctuate in a significant fraction of patients with SLE. Shown are R-C4d levels of 64 patients with SLE examined at 3 up to 5 different study visits. In 37 patients, R-C4d remained stably low. In 9 patients, R-C4d was elevated at the first visit, but decreased in subsequent visits. Remarkable fluctuation of R-C4d was observed in 18 patients. Representative patients with different patterns of R-C4d were selected for the case studies shown in FIG. 5A-D.

[a] Values given as mean ± SD, range
[b] A clinical manifestation is recorded positive if ever present since the diagnosis of SLE in individual patients; % of patients with a positive history of the indicated manifestation, unless otherwise specified
[c] % of patients with positive anti-dsDNA, or below normal levels of serum C3 or C4 at the time of the study visit (n = 155)
[d] SLAM (Systemic Lupus Activity Measure) and SELENA-SLEDAI (Safety of Estrogens in Lupus Erythematosus National Assessment version of the Systemic Lupus Erythematosus Disease Activity Index)
[e] SLAM or SLEDAI score at the time of the study visit Comparison of C4d Levels on Reticulocytes Among Study Participants Previous studies by us (Manzi S et al., *Arthritis Rheum.*, 50:3596-3604 (2004)) and others (Tieley C A et al., *Nature*, 276:713-715 (1978); Atkinson J P et al., *Complement*, 5:65-76 (1988)) have shown the presence of C4d, a complement activation product, on the surface of erythrocytes. To evaluate the potential of R-C4d as a biomarker of disease activity, we first demonstrate C4d deposition on reticulocytes. Using a 2-color flow cytometric assay, we conducted a cross-sectional study to examine and compare the presence of C4d on reticulocytes of healthy individuals, patients with SLE, and patients with other diseases. Initial studies showed that variable yet generally low levels of C4d could be detected on reticulocytes (R-C4d) of all healthy controls and most patients with other diseases (FIG. 4A and Table 2). In contrast, significantly elevated levels of C4d were detected on reticulocytes of many patients with SLE (FIG. 4A). When the R-C4d specific median fluorescence levels were compiled for the entire study population, the mean R-C4d level of SLE patients (5.50+/−9.01; range: 0-66.81) was significantly higher than those found in healthy controls (p<0.0001) or patients with other diseases (p<0.0001) (Table 4).

Figure 4B:
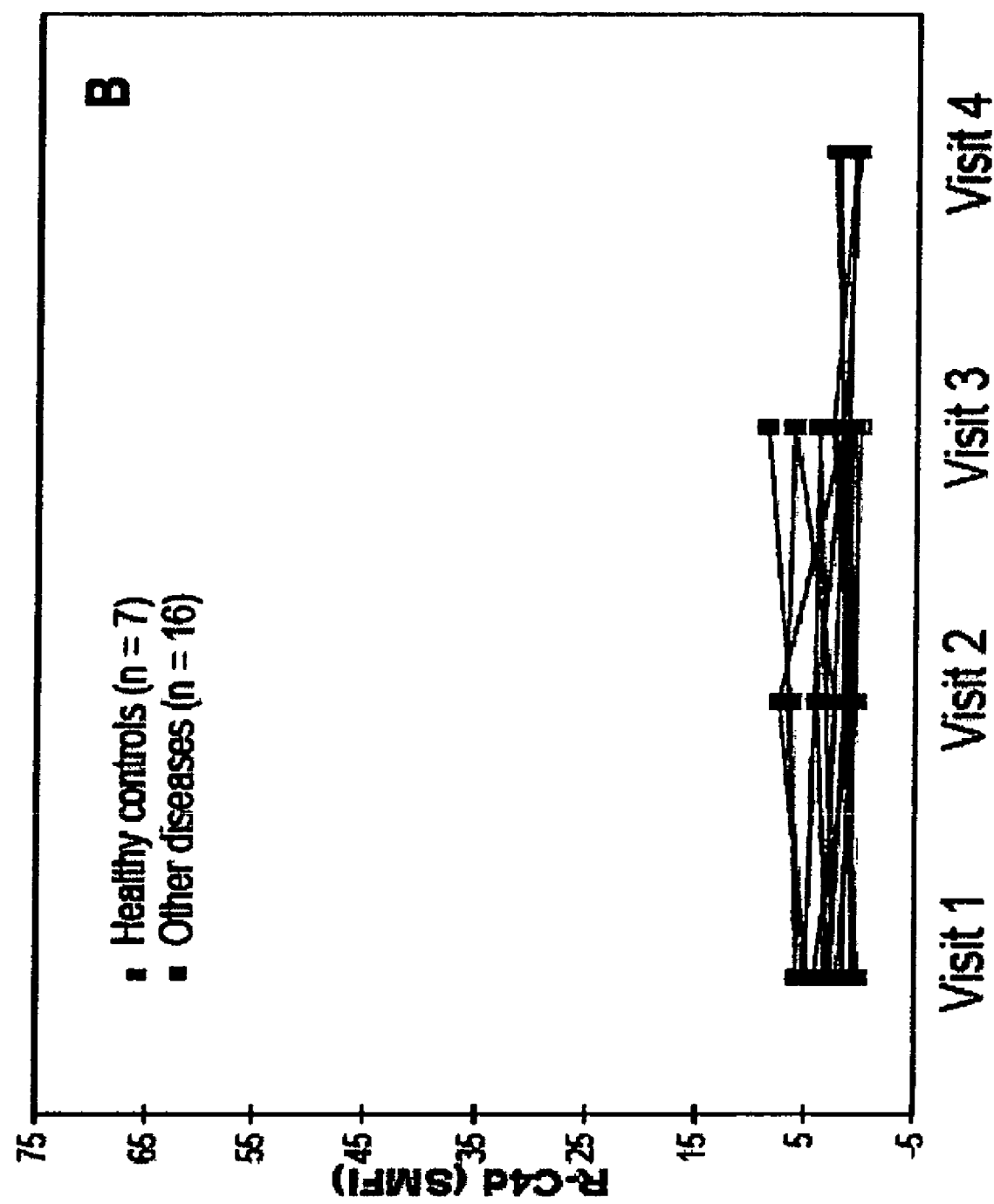
Figure 4C:
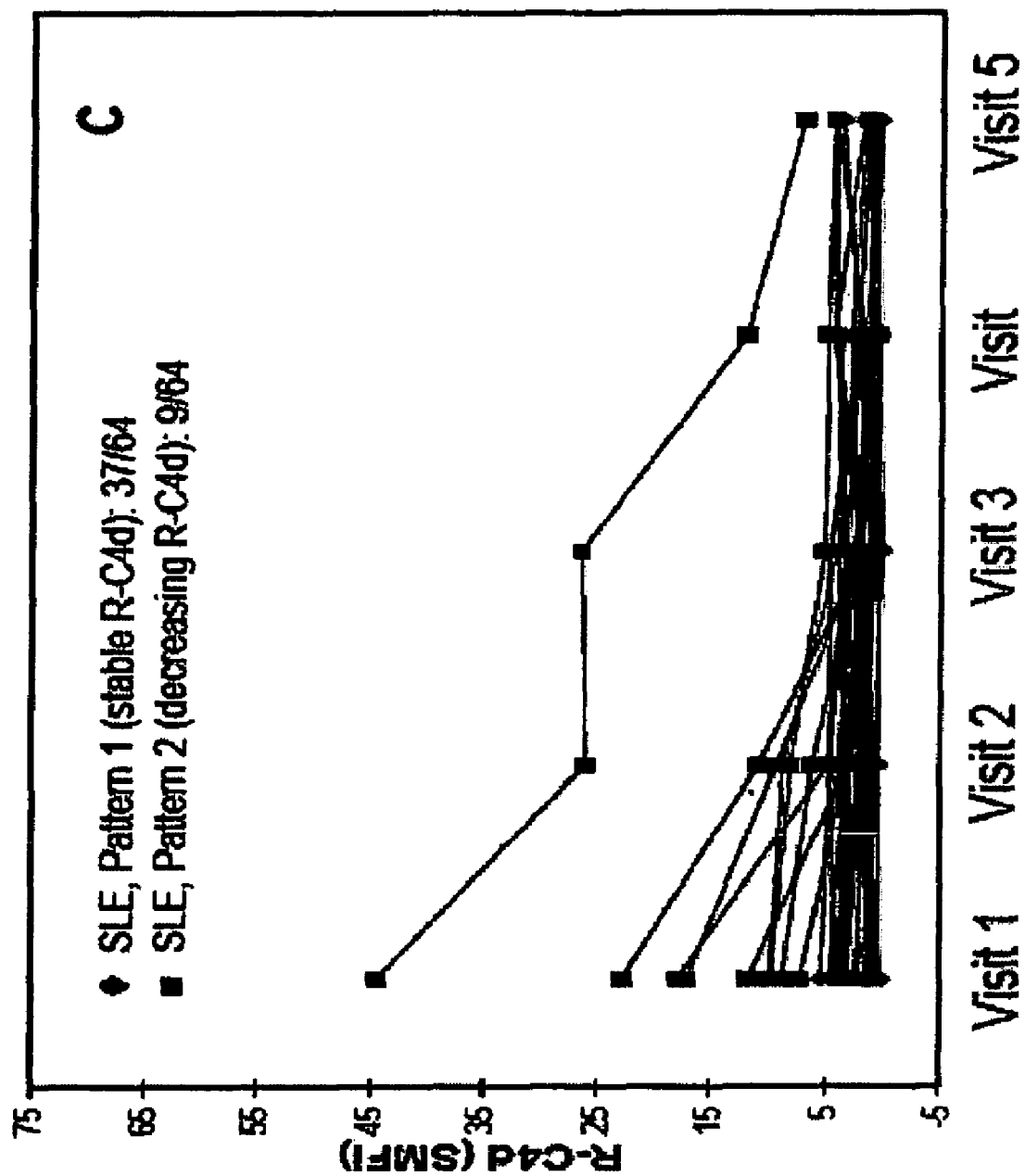
Figure 4D:
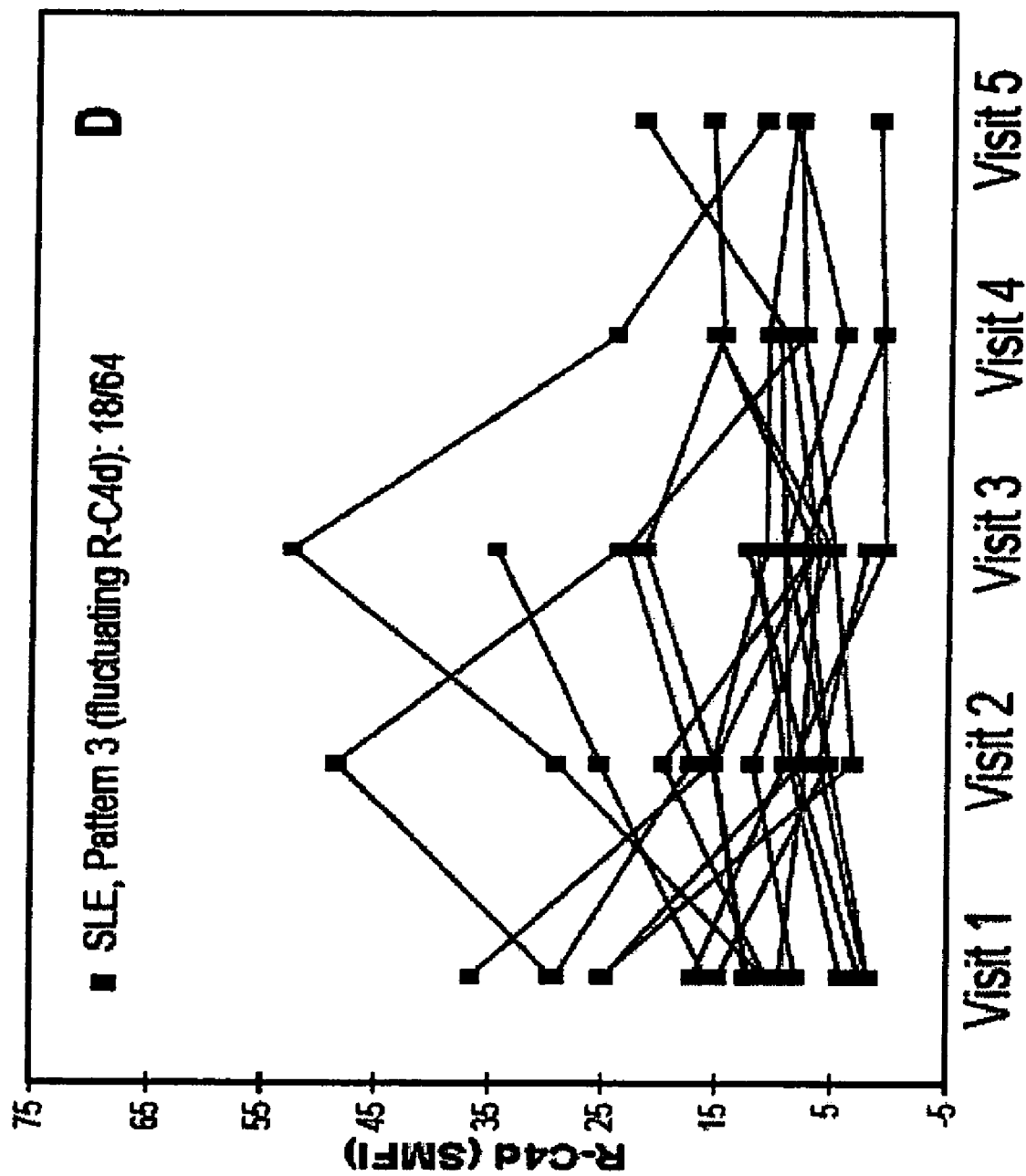

The R-C4d levels remained relatively constant in the healthy controls and patients with other diseases as shown by longitudinal study. FIG. 4B summarizes results obtained from representative healthy controls and patients with other diseases, with remarkably similar R-C4d levels over days, months, and years. However, the R-C4d levels in a significant fraction of SLE patients varied considerably over time (FIGS. 4C and 4D).

Correlation Between R-C4d Levels and SLE Disease Activity

Our cohort of SLE patients representing a wide range of disease activity enabled us to determine the capacity of R-C4d to reflect disease activity during a single clinic visit. Both disease activity indices were significantly associated with R-C4d, although the correlation with the SELENA SLEDAI ($r=0.45$, $p<0.00001$) was better than the SLAM ($r=0.23$, $p=0.003$). For an additional analysis, we ranked and sorted the SLE study participants into 4 increment groups according to their R-C4d levels, with patients in the bottom quartile having the lowest R-C4d levels. The disease activity of each patient at the study visit was determined using the SELENA-SLEDAI and the SLAM disease activity indices (Table 5). Other laboratory parameters that may reflect lupus disease activity (e.g., anti-dsDNA, complete blood counts, serum complement levels) were also examined in relationship to the quartiles of R-C4d.

TABLE 4

Comparison of Reticulocyte-and Erythrocyte-bound C4d levels* in patients with SLE, patients with other diseases, and healthy controls

|  | R-C4d mean +/− SD (median; range) p value[a,b] | E-C4d mean +/− SD (median; range) p value[a,b] |
|---|---|---|
| SLE (n = 156) | 5.50 +/− 9.00 (2.30; 0-66.8) | 18.36 +/− 27.92 (9.58; 0.5-22.7) |
| Other Diseases (n = 140) | 1.79 +/− 2.12 (1.26; 0-17.6) <0.0001[a] | 7.21 +/− 7.50 (4.93; 0.4-47) <0.0001[a] |
| Healthy Controls (n = 159) | 1.4 +/− 0.72 (0.85; 0-4.68) <0.0001[b] | 4.30 +/− 3.51 (3.42; 0-27) <0.0001[b] |

*Data shown represent C4d-specific median fluorescence intensity (SMFI).
[a]Differences between patients with SLE and patients with other diseases analyzed by Wilcoxon rank sum test
[b]Differences between patients with SLE and healthy controls analyzed by Wilcoxon rank sum test.

TABLE 5

Correlation between R-C4d, E-C4d, and SLE Disease Activity

| Patient Group (n = 39/group) | SLEDAI mean +/− SD | p value | SLAM mean +/− SD | p value | % Positive Anti-dsDNA | % Anemia (Hct <35) | % Thrombocytopenia (Plt <150000) |
|---|---|---|---|---|---|---|---|
| 1st quartile (R-C4d 0-1.12) | 1.36 +/− 1.35 |  | 4.64 +/− 2.41 |  | 24 | 20 | 0 |
| 2nd quartile (R-C4d 1.12-2.31) | 2.64 +/− 3.11 | 0.022[a] | 5.26 +/− 3.48 | N.S[a] | 30 | 26 | 10 |
| 3rd quartile (R-C4d 2.31-4.85) | 2.85 +/− 1.87 | 0.0001[b] | 6.20 +/− 4.28 | N.S[b] | 54 | 33 | 15 |
| 4th quartile (R-C4d 4.85-66.8) | 4.34 +/− 3.84 | 0.00002[c] | 7.08 +/− 4.18 | 0.02[c] | 56 | 50 | 18 |
|  | P < 0.0001[d] |  | P < 0.0001[d] |  | p = 0.007[d] | p = 0.025[d] | p = 0.016[d] |
| 1st quartile (E-C4d 0-5.1) | 1.64 +/− 2.37 |  | 4.97 +/− 2.92 |  | 29 | 21 | 0 |
| 2nd quartile (E-C4d 5.1-9.6) | 2.46 +/− 2.27 | N.S[a] | 5.48 +/− 3.11 | N.S[a] | 28 | 31 | 15 |
| 3rd quartile (E-C4d 9.6-17.9) | 3.23 +/− 2.92 | 0.002[b] | 6.26 +/− 4.23 | N.S[b] | 54 | 23 | 10 |
| 4th quartile (E-C4d 17.9-227) | 3.95 +/− 4.44 | <0.001[c] | 6.46 +/− 4.44 | N.S.[c] | 53 | 41 | 18 |
|  | P < 0.001[d] |  | N.S.[d] |  | P = 0.02[d] | P = 0.20[d] | P = 0.059[d] |

[a]1st quartile vs. 2nd quartile; Wilcoxon rank sum test
[b]1st quartile vs. 3rd quartile; Wilcoxon rank sum test
[c]1st quartile vs. 4th quartile; Wilcoxon rank sum test
[d]Significance of trend in increasing analyzed by chi square test for trend
N.S.: not significant When the disease activity scores of all SLE patients were compiled, the median SELENA-SLEDAI scores were significantly different among the 4 groups in pair-wise comparison (p=0.022; p=0.0001; p=0.00002) (Table 5). The median SLAM scores also differed among the 4 groups, although the differences were statistically significant only between the SLE patients in the top quartile with the highest R-C4d levels and those in the bottom quartile with the lowest R-C4d levels (p<0.02). R-C4d was also observed to correlate significantly with specific disease variables including anti-dsDNA (p=0.007), anemia (p<0.025), and thrombocytopenia (p<0.016).

In comparison, E-C4d was significantly associated with SELENA-SLEDAI (r=0.37, p<0.00001), although not as strongly as R-C4d (r=0.46, p<0.00001). E-C4d was not significantly associated with the SLAM (r=0.14, p=0.07). This is also demonstrated in Table 5, when the disease activity scores were compiled in SLE patients ranked according to their E-C4d levels.

Example 3

Correlation Between R-C4d Levels and SLE Disease Activity, Case Studies

R-C4d levels in healthy controls and in patients with other diseases were low and stable over time (FIG. 4B). In contrast, we observed three patterns in patients with SLE. The first group of patients had stable low levels of R-C4d (FIG. 4C). The second group of patients had a significantly elevated R-C4d level at the first visit, which decreased in subsequent visits (FIG. 4C). The third group of patients had R-C4d levels that fluctuated over time (9-26 months).

The following four case reports are presented to demonstrate the capacity of R-C4d to fluctuate with the clinical course of SLE. In these illustrative examples, R-C4d measurement is compared with two "gold standard" laboratory tests used in clinical care of patients with SLE: serum C4 and dsDNA antibody titer, with the two disease activity indices SLAM and SLEDAI, and with ESR, a non-specific measure of systemic inflammation. In addition, we compare the utility of E-C4d with R-C4d.

Figure 5A:
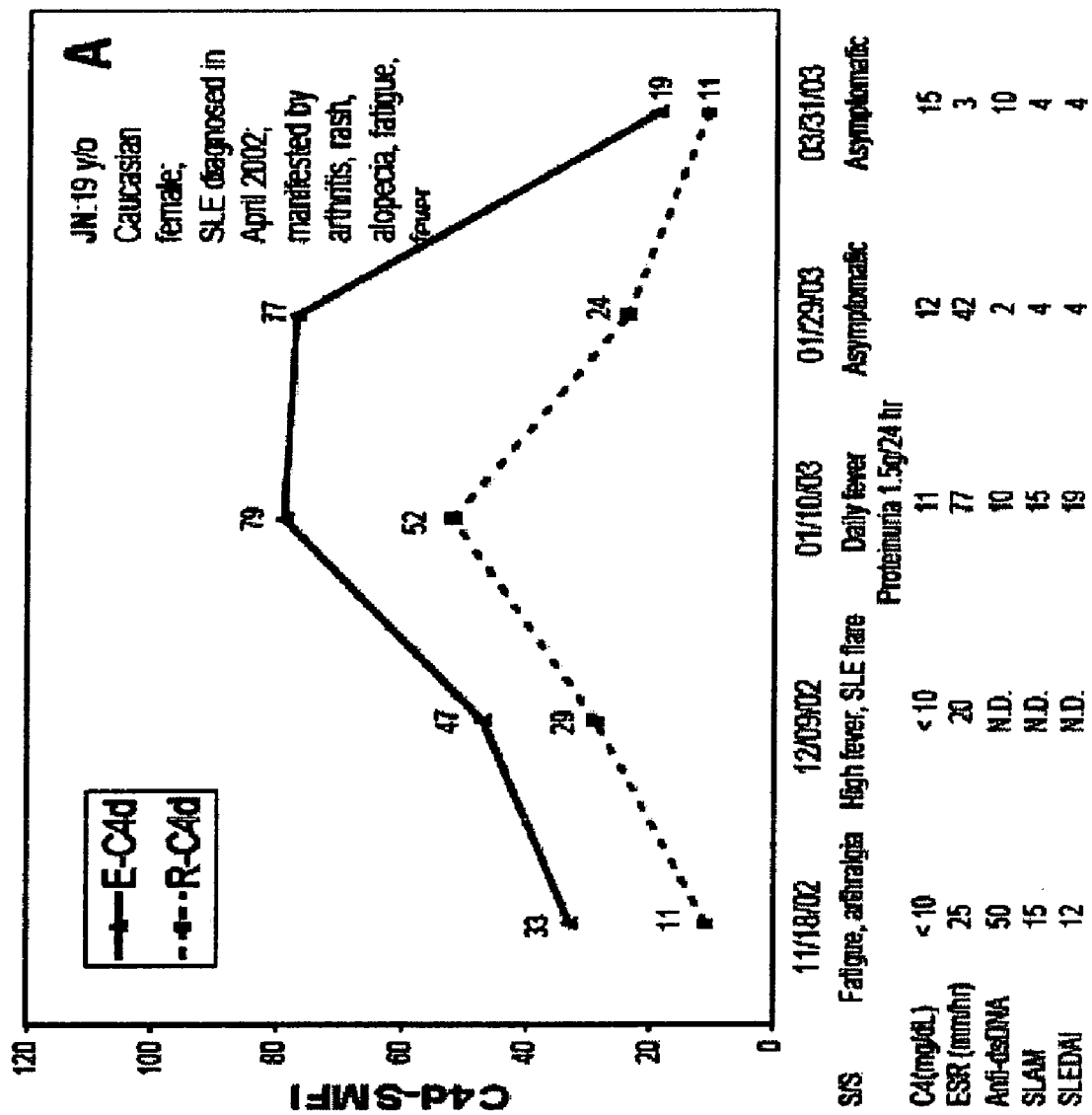
FIG. 5A-D demonstrates that R-C4d fluctuates and reflects the clinical course of SLE. Shown are serial measurements of Reticulocyte-C4d (R-C4d) and Erythrocyte-C4d (E-C4d) from each representative patient with SLE. Numbers shown inside the graph panel near each point are values of C4d-specific median fluorescence intensity. See Example 4 for additional clinical history and results of other laboratory tests. Normal lab values are: serum C4 level is 20-59 mg/dL; ESR 0-20 mm/hr; fanti-dsDNA <2 or <1:10, depending on the type of assay used.

Case A: Patient JN is a 19-year-old Caucasian woman diagnosed with SLE in April of 2002. Her SLE was manifested by inflammatory arthritis, rash, alopecia, oral ulcers, fatigue, fevers, presence of anti-nuclear antibody [1:320, homogeneous pattern], anti-double stranded DNA antibody [50; normal <2], anti-cardiolipin antibody [IgG, 29], and slightly elevated ESR [28 mm/hr; normal 0-20]. She was noncompliant with her medications (hydroxychloroquine and methotrexate) and was taking only prednisone 5 mg/day at the time of her first study visit on Nov. 18, 2002 (FIG. 5A). At this visit, she complained of fatigue, and had evidence of active arthritis and oral ulcers. Her laboratory tests showed undetectable serum C4 [<10], slightly elevated ESR [25 mm/hr], and anti-dsDNA [50]; R-C4d [11] and E-C4d [33] levels were both elevated. The patient was restarted on hydroxychloroquine and methotrexate. JN presented to the emergency room with high fever and headache in December 2002, at which time her serum C4 remained undetectable and ESR had decreased to 20 mm/hr. In contrast, R-C4d [29] and E-C4d [47] both increased significantly, suggesting an increase in disease activity. Anti-dsDNA was not determined. She was admitted to the hospital. A thorough evaluation for infection was negative. She was discharged with no change in therapy. On Jan. 10, 2003, JN was hospitalized for newly developed proteinuria, renal insufficiency, and worsening of constitutional symptoms. A diagnosis of mesangial glomerulonephritis was rendered after a renal biopsy. At this time, serum C4 was now increased to a detectable level [11] and anti-dsDNA titer was decreased to 10, both laboratory tests suggesting possible improvement or no change in lupus activity. In contrast, E-C4d [79] and R-C4d [52] had increased markedly by this time, suggesting a disease flare that was consistent with the clinical impression and with the renal biopsy. After intensive treatment with a 3-day pulse of 1000 mg of Solumedrol followed by oral prednisone, hydroxychloroquine, and mycophenolate mofetil (CellCept), JN's condition improved, with decrease in serum creatinine level [1.2 to 0.7 mg/dL] and resolution of fever and arthralgia. By Jan. 29, 2003, her R-C4d level had decreased from 52 to 24, whereas E-C4d did not change significantly [79 to 77]. In contrast, serum C4 remained low and not significantly changed [12]. The clinical impression was improvement and response to intervention, which, despite elevated E-C4d [77], ESR [42], and abnormal C4 [12], was consistent with marked decrease in R-C4d. Her prednisone dose was lowered. This impression was confirmed on Mar. 31, 2003, at which time the patient returned without symptoms. By this time, R-C4d and E-C4d had decreased to 11 and 19, respectively. However, C4 remained low at 15 and anti-dsDNA was increased at 10, the same value observed at the peak of the flare on January 10.

Figure 5B:
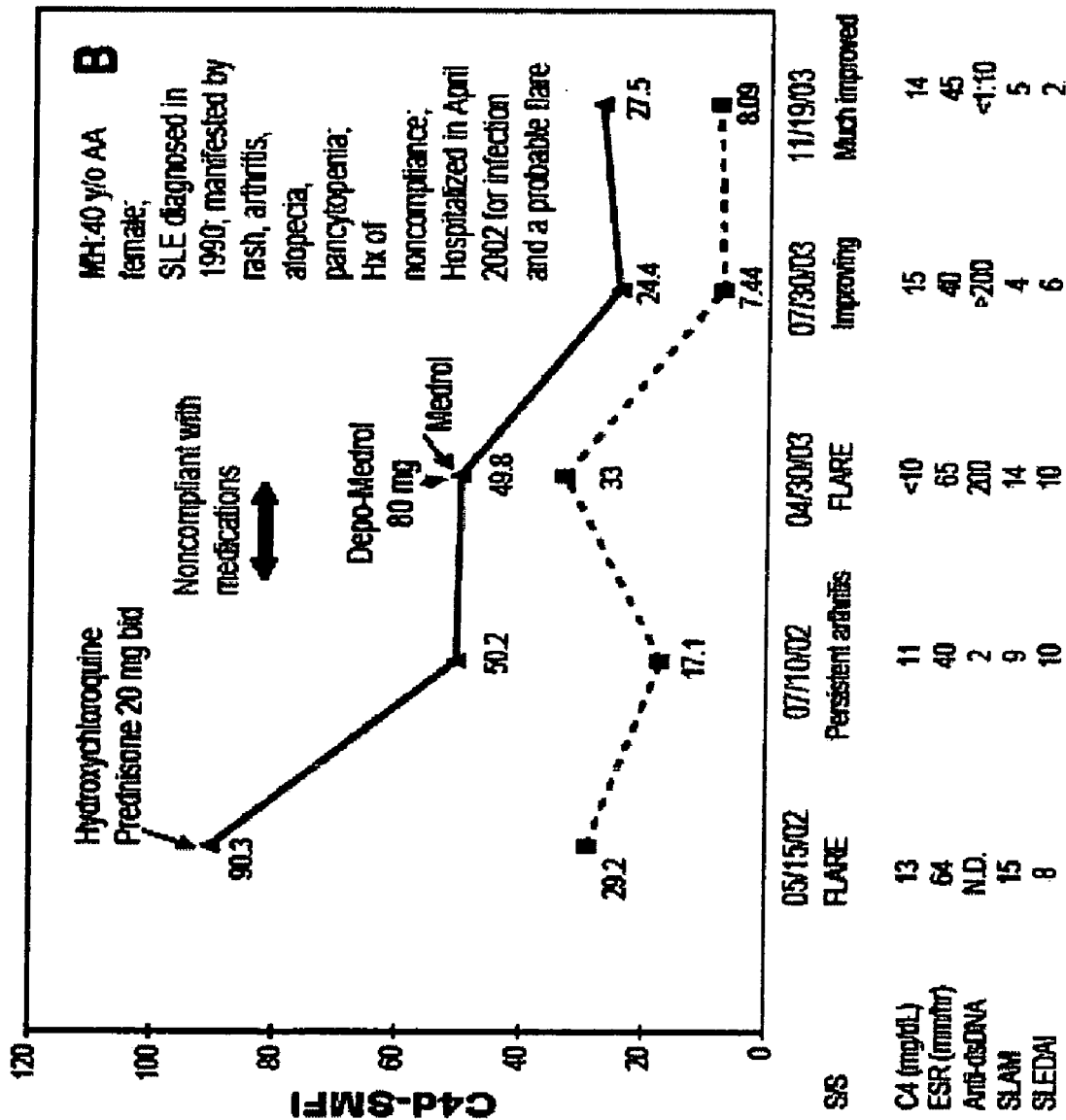

Case B: Patient MH, is a 40 year-old African American woman who was diagnosed with SLE in 1990 and has a history of noncompliance with medications. She was hospitalized for an ear infection and worsening arthritis a few weeks prior to her first study visit in May 2002. By the time of the first study visit, her symptoms had improved on 40 mg/day prednisone. The detection of markedly elevated E-C4d [90] and moderately high R-C4d [29] levels, were consistent with a recent flare. Response to therapy was confirmed by significantly reduced E-C4d and R-C4d levels at the next visit in July 2002. At the third study visit in April 2003, MH was experiencing worsening arthritis and skin rash. She reported noncompliance with all medications during the preceding two months. At that time, her R-C4d level was significantly elevated as compared to the previous visit, consistent with her reported flare, which was successfully treated with an injection of Depo-Medrol followed by oral Medrol. She reported marked resolution of all symptoms during the subsequent several months, consistent with R-C4d levels in the normal range (FIG. 5B).

Figure 5C:
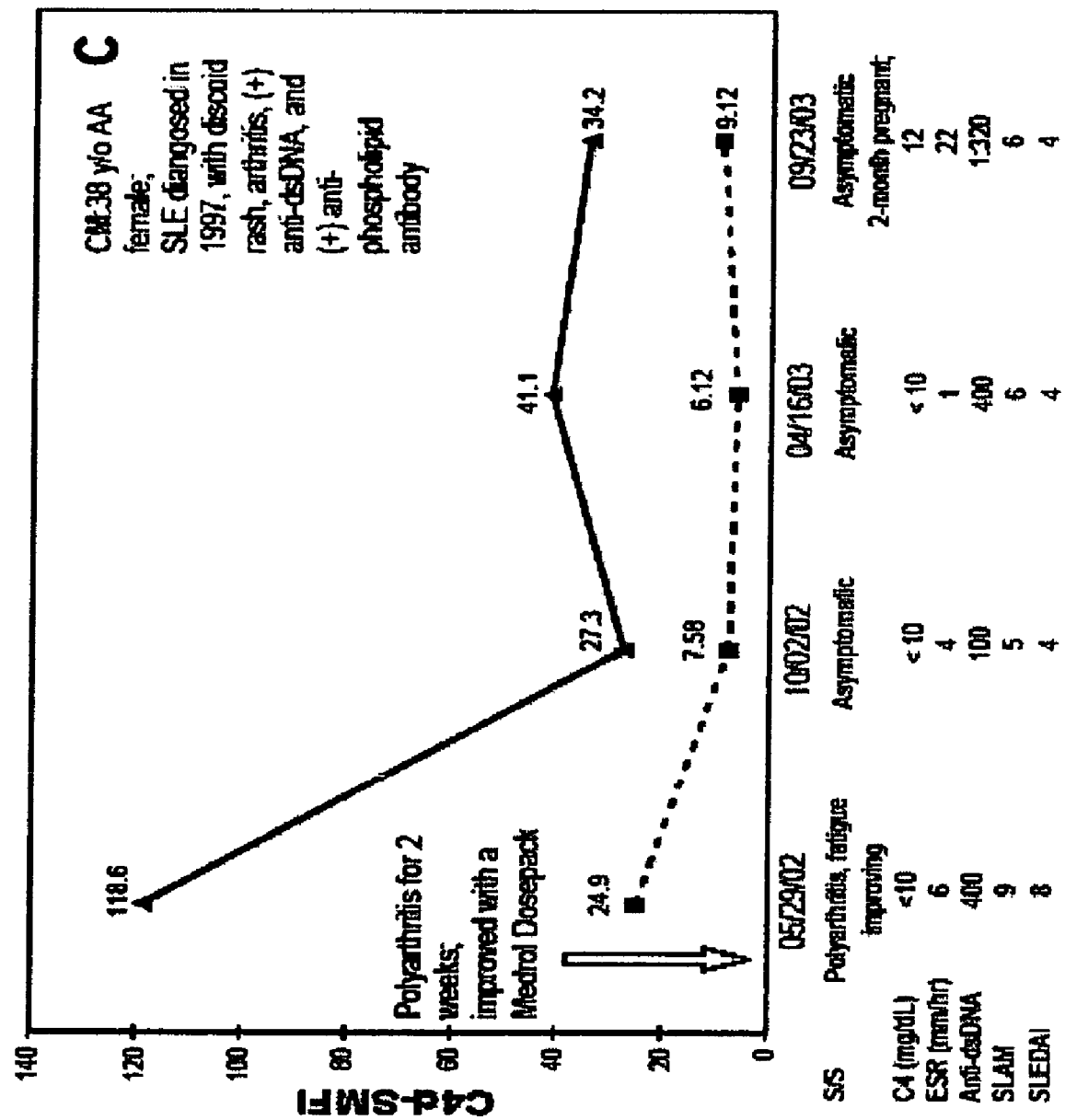

Case C: Patient CM is a 38-year-old African American woman with SLE diagnosed in 1997 and manifested by discoid lesions, arthritis, and anti-phospholipid antibody syndrome. In April 2002, CM reported a 2-week history of flare manifested by polyarthritis. This was treated with a Medrol dose pack. The patient reported marked improvement by the time of her first study visit in May 2002, and she subsequently remained asymptomatic (FIG. 5C). R-C4d levels decreased with response to therapy and remained low during the 16-month asymptomatic interval, despite persistently positive anti-dsDNA and abnormally low serum C4.

Figure 5D:
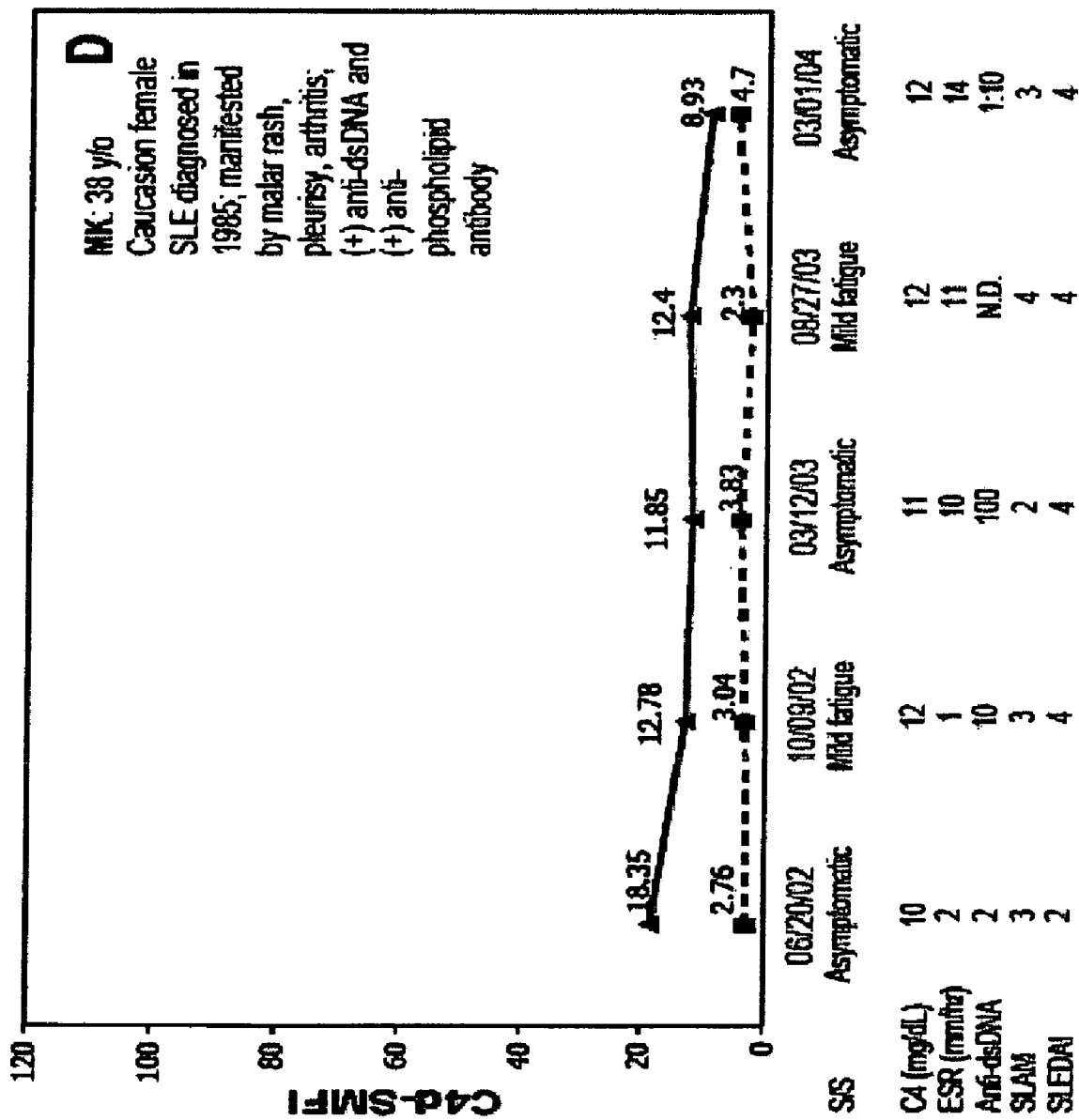

Case D: Patient MK is a 38-year-old Caucasian woman with SLE diagnosed in 1985 and manifested by malar rash, photosensitivity, arthritis, and pleurisy. During five study visits spanning 20 months, she remained asymptomatic. R-C4d levels remained normal, despite abnormal levels of serum C4 and fluctuating anti-dsDNA positivity (FIG. 5D).

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

All publications and patent applications cited in this specification are herein incorporated by reference as if each individual publication or patent application were specifically and individually indicated to be incorporated by reference.

What is claimed is:

1. A method for diagnosing an acute inflammatory episode of systemic lupus erythematosus (SLE) in an individual, the method comprising:
   (a) isolating reticulocytes from a blood sample of an individual;
   (b) determining the level of a C4d complement pathway component on the isolated reticulocytes from the individual, and
   (c) comparing the C4d complement pathway component level on the isolated reticulocytes from the individual with a control level of C4d complement pathway component on reticulocytes, wherein an elevated level of the C4d complement pathway component on the isolated reticulocytes in the individual compared to the control level of the C4d complement pathway component on reticulocytes indicates that the individual has the acute inflammatory episode of SLE.

2. The method of claim 1, wherein the level of the C4d complement pathway component is determined using an antibody specific for the C4d complement pathway component.

3. The method of claim 2, wherein the C4d antibody is labeled.

4. The method of claim 3, wherein the C4d antibody is detected using flow cytometric analysis.

5. A method of predicting an acute inflammatory episode of systemic lupus erythematosus (SLE) in an individual, the method comprising:
   (a) isolating reticulocytes from a blood sample of an individual;
   (b) determining the level of a C4d complement pathway component on the isolated reticulocytes from the individual, and
   (c) comparing the C4d complement pathway component level on the isolated reticulocytes from the individual with a control level of complement pathway component on reticulocytes, wherein an elevated level of the C4d complement pathway component in the isolated reticulocytes in the individual compared to the control level of the C4d complement pathway component on reticulocytes is predictive of an acute inflammatory episode of SLE.

6. The method of claim 5, wherein the level of the C4d complement pathway component is determined using an antibody specific for the C4d complement pathway component.

7. The method of claim 6, wherein the C4d antibody is labeled.

8. The method of claim 7, wherein the C4d antibody is detected using flow cytometric analysis.

9. A method for monitoring the clinical course of an acute inflammatory episode of systemic lupus erythematosus (SLE), the method comprising:
   (a) isolating reticulocytes from a blood sample of an individual at a first time point and at a second time point;
   (b) determining the level of a C4d complement pathway component on the isolated reticulocytes of the individual at the first time point; and
   (c) comparing the level of the C4d complement pathway component on the isolated reticulocytes of the individual at the first time point with the isolated reticulocytes of the individual at the second time point, wherein a change in the level of the C4d complement pathway component on the isolated reticulocytes from the first time point to the second time point of the individual indicates a change in the clinical course of the acute inflammatory episode of SLE in the individual.

10. The method of claim 9, wherein the level of the C4d complement pathway component is determined using an antibody specific for the C4d complement pathway component.

11. The method of claim 10, wherein the C4d antibody is labeled.

12. The method of claim 11, wherein the C4d antibody is detected using flow cytometric analysis.

* * * * *